(12) United States Patent
Ishida et al.

(10) Patent No.: US 6,221,264 B1
(45) Date of Patent: Apr. 24, 2001

(54) WHITE BLOOD CELL-REMOVING DEVICE, WHITE BLOOD CELL-REMOVING APPARATUS AND WHITE BLOOD CELL-REMOVING METHOD

(75) Inventors: Noboru Ishida; Susumu Fujikawa, both of Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/314,082

(22) Filed: May 19, 1999

(30) Foreign Application Priority Data

May 19, 1999 (JP) .................................... 10-155232

(51) Int. Cl.$^7$ .................................... B01D 37/00
(52) U.S. Cl. ............... 210/767; 210/416.1; 210/448; 210/483; 604/406; 604/408; 604/410
(58) Field of Search ................. 210/257.1, 406, 210/416.1, 436, 448, 472, 645, 767, 483, 452, 806; 604/319, 406, 408, 409, 410

(56) References Cited

U.S. PATENT DOCUMENTS

| | | | | |
|---|---|---|---|---|
| 3,593,854 | * | 7/1971 | Swank | 210/436 |
| 4,437,472 | * | 3/1984 | Naftulin | 604/408 |
| 4,466,888 | * | 8/1984 | Verhart | 604/406 |
| 5,180,504 | | 1/1993 | Johnson et al. | 210/767 |
| 5,269,924 | * | 12/1993 | Rochat | 604/406 |
| 5,527,472 | | 6/1996 | Belloti et al. | 210/767 |
| 5,543,062 | * | 8/1996 | Nishimura | 210/767 |
| 5,601,730 | | 2/1997 | Page et al. | 210/806 |
| 5,632,906 | * | 5/1997 | Ishida | 210/767 |
| 5,695,489 | * | 12/1997 | Japunitch | 604/406 |
| 5,792,133 | * | 8/1998 | Rochat | 604/406 |
| 5,911,886 | * | 6/1999 | Delmar | 210/767 |
| 5,938,940 | * | 8/1999 | Zuk | 210/767 |

FOREIGN PATENT DOCUMENTS

| | | |
|---|---|---|
| 2677883 | 12/1992 | (FR) . |
| 516846 | 12/1992 | (EP) . |
| 2695037 | 3/1994 | (FR) . |
| 57-10856 | 1/1982 | (JP) . |
| 94/01193 | 1/1994 | (WO) . |
| 94/28996 | 12/1994 | (WO) . |
| 95/17236 | 6/1995 | (WO) . |

\* cited by examiner

*Primary Examiner*—Joseph W. Drodge
(74) *Attorney, Agent, or Firm*—Burns, Doane, Swecker & Mathis, LLP

(57) ABSTRACT

A white blood cell-removing device has a bag-shaped housing made of soft resin, a white blood cell-removing filter member partitioning the inside of the housing into an inlet side blood chamber and an outlet side blood chamber, a blood inlet port positioned at one side of the housing and communicating with the inlet side blood chamber; and a blood outlet port positioned at the other side of the housing and communicating with the outlet side blood chamber. An inner surface (the outlet side blood chamber) of the bag-shaped housing is a unevenness surface. The white blood cell-removing filter member has a filtering part and a non-filtering part formed on the entire periphery of the filtering part.

24 Claims, 16 Drawing Sheets

WHITE BLOOD CELL-REMOVING DEVICE, WHITE BLOOD CELL-REMOVING APPARATUS AND WHITE BLOOD CELL-REMOVING METHOD

BACKGROUND OF THE INVENTION

The present invention relates to a white blood cell-removing device to be used in obtaining a blood product not containing white blood cells or other blood components contained in blood collected from a donor. The present invention also relates to a white blood cell-removing apparatus and a white blood cell-removing method for obtaining the blood product not containing white blood cells or other blood components contained in the blood collected from the donor.

Generally, the white blood cell-removing device has a housing; a white blood cell-removing filter provided to partition the inside of the housing into an inlet side blood chamber and an outlet side blood chamber; a blood inlet port communicating with the inlet side blood chamber; and a blood outlet port communicating with the outlet side blood chamber.

The white blood cell-removing device is used by connecting a tube provided at a blood inlet side with a tube of a container accommodating non-filtered blood and connecting a tube provided at a blood outlet side with a tube of a container accommodating filtered blood. White blood cells are removed by placing the container accommodating the non-filtered blood at an upward position, the container accommodating the filtered blood at a downward position, and the white blood cell-removing device at a position intermediate therebetween to introduce blood into the white blood cell-removing device by utilizing the vertical difference between the positions thereof. White blood cell-removed blood is accommodated in the container located at the downward position.

When the white blood cell-removing device has a construction containing much air therein, the air prevents a smooth flow of blood. To expel the air from the white blood cell-removing device, an air-removing operation is performed by placing the inlet side of the white blood cell-removing device at a downward position and the outlet side thereof at an upward position; and then, the white blood cell-removing device is turned upside down to perform a filtering operation.

A smooth filtration proceeds for a certain period of time after the blood filtering operation starts. But after a while, the filtering speed becomes very slow. Because the amount of unfiltered blood injected into the inlet side of the white blood cell-removing device is small immediately after the blood filtering operation starts, a low pressure is applied to a filtering material and thus the flow-down speed of the blood is not reduced. In the case of a white blood cell-removing device having a housing made of a soft material, shortly after blood more than an amount corresponding to the volume of the inlet side blood chamber is injected thereinto, the filtering material is pressed by the pressure of the blood which has been stored in the inlet side blood chamber. As a result, the volume of the outlet side blood chamber decreases and the filtering material contacts the inner surface of the housing made of the soft material. Consequently, the outlet side blood chamber is closed and the filtering speed becomes very slow.

As a container for collecting filtered blood, a soft blood bag is generally used. After the filtering operation starts, an initial flow of filtered blood flowing out from a white blood cell-removing device drops to a filtered blood collection container at a speed nearly equal to a free drop speed. This is because there are no factors which prevent the drop of the filtered blood below the white blood cell-removing device. But when the flow speed of the filtered blood is low at the outlet side of the filter, as described above, the filtered blood collection container acts as though it pulls the filtered blood thereto. As a result, the outlet side blood chamber of the white blood cell-removing device has a negative pressure, which allows the housing made of the soft material to contact the filtering material closely.

A long filtering time leads to deterioration of not only operability but also the quality of the blood product.

In order to solve such a problem, there is proposed a method of inserting a separate member, for example, a space-forming material or a rod into the outlet side blood chamber. But the insertion of the separate member may cause a defective adhesion of the material of the housing, which causes leak of blood.

The following method has been also adopted to obtain a blood product: an unprocessed blood filling container is connected with the blood inlet port of a white blood cell-removing device; a processed blood collection container is connected with the blood outlet port of the white blood cell-removing device; and the unprocessed blood filling container is placed at an upward position and the processed blood collection container is placed at a downward position to collect processed blood by gravity by the processed blood collection container.

But the above method has a problem that at the termination of the white blood cell-removing, it is impossible to collect blood remaining in the interior of the white blood cell-removing device, blood remaining in a tube between the white blood cell-removing device and the unprocessed blood filling container, and blood remaining in a tube between the white blood cell-removing device and the processed blood collection container.

Therefore, it is a first object of the present invention to provide a white blood cell-removing device not using a separate member to prevent defective adhesion of materials of a housing thereof and having a blood filtering speed which is reduced in a small extent.

It is a second object of the present invention to provide a white blood cell-removing apparatus and a white blood cell-removing method capable of obtaining much blood product from collected blood.

SUMMARY OF THE INVENTION

In a first aspect, the present invention provides a white blood cell-removing device comprising a bag-shaped housing made of soft resin; a white blood cell-removing filter member partitioning an inside of said housing into an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, wherein an unevenness surface having a difference of 0.2–2 mm between highest and lowest portions thereof is formed on an inner surface of said bag-shaped housing made of soft resin and confronting said outlet side blood chamber, and wherein said white blood cell-removing filter member has a filtering part and a non-filtering part formed on an entire periphery of said filtering part; and a blood duct formed between said non-filtering part and an inner surface of said housing is located on an inner peripheral part of said housing.

In a second aspect, the present invention provides a white blood cell-removing apparatus comprising a white blood cell-removing device comprising a housing made of soft resin, a white blood cell-removing member partitioning an inside of said housing into an inlet side blood chamber and an outlet side blood chamber, a blood inlet port positioned at one side of said housing and communicating with said inlet side blood chamber and a blood outlet port positioned at the other side of said housing and communicating with said outlet side blood chamber; a first tube connecting to said blood inlet port; a processed blood collection container made of soft resin; and a second tube connecting said processed blood collection container and said blood outlet port with each other, wherein said processed blood collection container contains air whose amount is equal to or more than the difference between a volume of blood filled in said outlet side blood chamber of said white blood cell-removing device and a volume of air preserved therein.

In a third aspect, the present invention provides a white blood cell-removing method which is carried out by using a white blood cell-removing device having: a bag-shaped housing made of soft resin; a white blood cell-removing member partitioning an inside of said housing into an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, said white blood cell-removing method being carried out in a state where an unprocessed blood filling container containing unprocessed blood is connected with said white blood cell-removing device at a blood flow inlet side thereof through a first tube, and a processed blood collection container made of soft resin and collecting treated blood is connected with said white blood cell-removing device at a blood flow outlet side thereof through a second tube, said method comprising the steps of: introducing blood into said white blood cell-removing device from said unprocessed blood filling container; feeding air inside said white blood cell-removing device to said processed blood collection container; feeding said blood contained in said unprocessed blood filling container to said processed blood collection container by passing said blood through said white blood cell-removing device; and feeding air in said processed blood collection container to said outlet side blood chamber of said white blood cell-removing device or/and to said second tube by pressing said processed blood collection container; and collecting processed blood in said outlet side blood chamber of said white blood cell-removing device or/and processed blood in said second tube into said processed blood collection container.

In a fourth aspect, the present invention provides a white blood cell-removing method which is carried out by using a white blood cell-removing device having: a bag-shaped housing made of soft resin; a white blood cell-removing member partitioning an inside of said housing into an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, said white blood cell-removing method being carried out in a state where an unprocessed blood filling container containing unprocessed blood is connected with said white blood cell-removing device at a blood flow inlet side thereof through a first tube, and a processed blood collection container collecting treated blood is connected with said white blood cell-removing device at a blood flow outlet side thereof through a second tube, said method comprising the steps of: pressing said white blood cell-removing device; feeding at least one part of air inside said white blood cell-removing device to said unprocessed blood filling container; collecting processed blood into said processed blood collection container by passing blood contained in said unprocessed blood filling container through said white blood cell-removing device. In a sixth aspect, the present invention provides a white blood cell-removing method which is carried out by using a white blood cell-removing apparatus comprising a white blood cell-removing device having: a bag-shaped housing made of soft resin; a white blood cell-removing member partitioning an inside of said housing into an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, said white blood cell-removing method being carried out in a state where an unprocessed blood filling container containing unprocessed blood is connected with said white blood cell-removing device at a blood flow inlet side thereof through a first tube, and a processed blood collection container made of soft resin and containing a blood-preserving liquid and collecting treated blood is connected with said white blood cell-removing device at a blood flow outlet side thereof through a second tube, said method comprising the steps of: feeding at least one part of said blood-preserving liquid from said processed blood collection container to said unprocessed blood filling container, together with at least one part of air in said white blood cell-removing device; feeding blood inside said unprocessed blood filling container to said processed blood collection container through said white blood cell-removing device; feeding air inside said processed blood collection container to said outlet side blood chamber of said white blood cell-removing device or/and to said second tube by pressing said processed blood collection container; and collecting processed blood present in said outlet side blood chamber of said white blood cell-removing device or/and processed blood present in said second tube into said processed blood collection container.

In a fifth aspect, the present invention provides a white blood cell-removing method which is carried out by using a white blood cell-removing device having: a bag-shaped housing made of soft resin; a white blood cell-removing member partitioning an inside of said housing into an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, said white blood cell-removing method being carried out in a state where an unprocessed blood filling container containing unprocessed blood is connected with said white blood cell-removing device at a blood flow inlet side thereof through a first tube; a processed blood collection container made of soft resin and containing a blood-preserving liquid and collecting treated blood is connected with said white blood cell-removing device at a blood flow outlet side thereof through a second tube, said method comprising the steps of: pressing said white blood cell-removing device to feed at least one part of air inside said white blood cell-removing device to said processed blood collection container in which said blood-preserving liquid has been filled; feeding blood inside said unprocessed blood filling container to said processed blood collection container through said white blood cell-removing device.

DETAILD DESCRIPTION OF THE PREFERRED EMBODIMENTS

Figure 1:
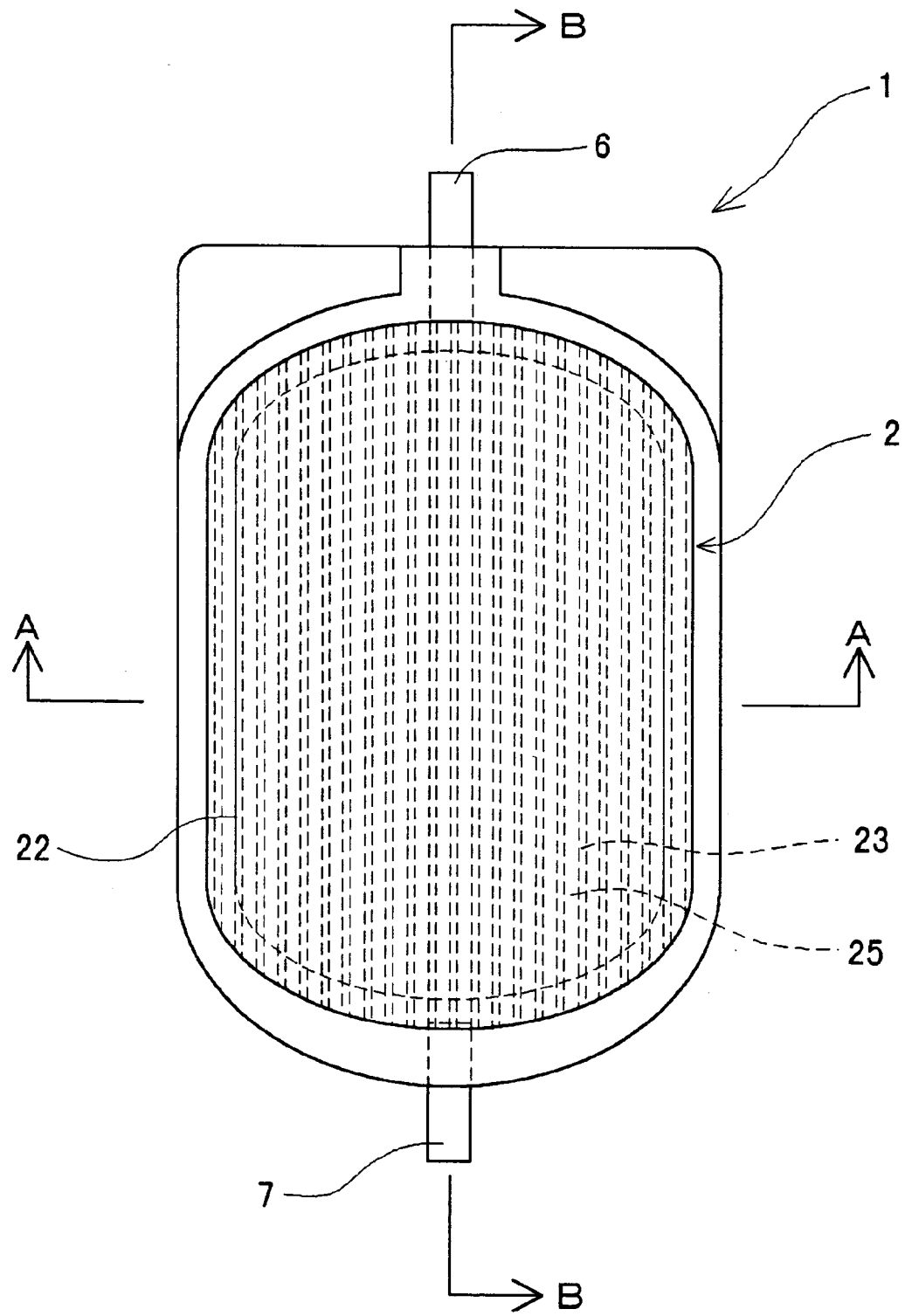
FIG. 1 is a front view showing a white blood cell-removing device of an embodiment of the present invention as viewed from an outlet side blood chamber thereof.

Using the embodiments shown in the drawings, the white blood cell-removing device of the present invention will be described below.

Figure 2:
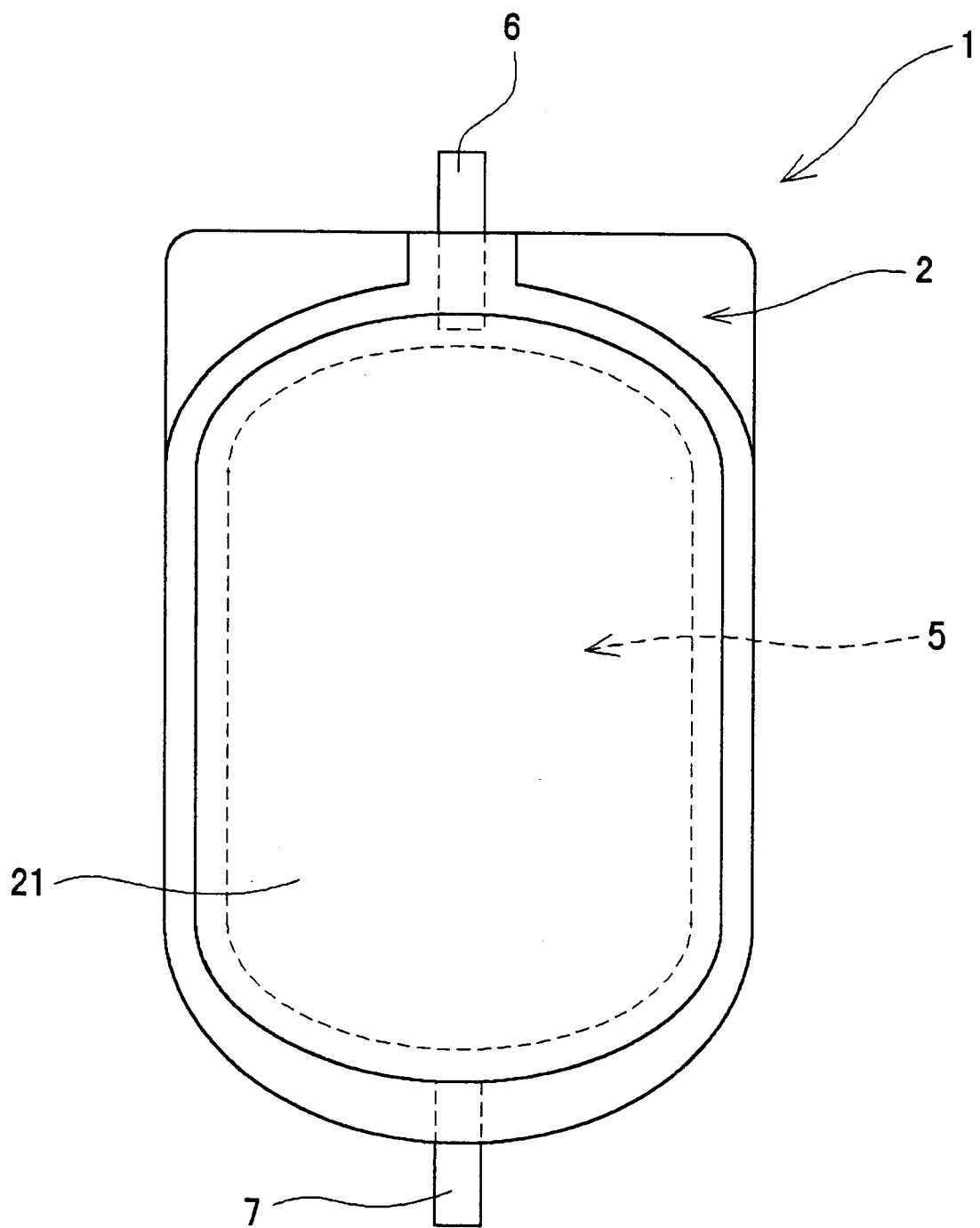
FIG. 2 is a rear view of the white blood cell-removing device of FIG. 1.
Figure 4:
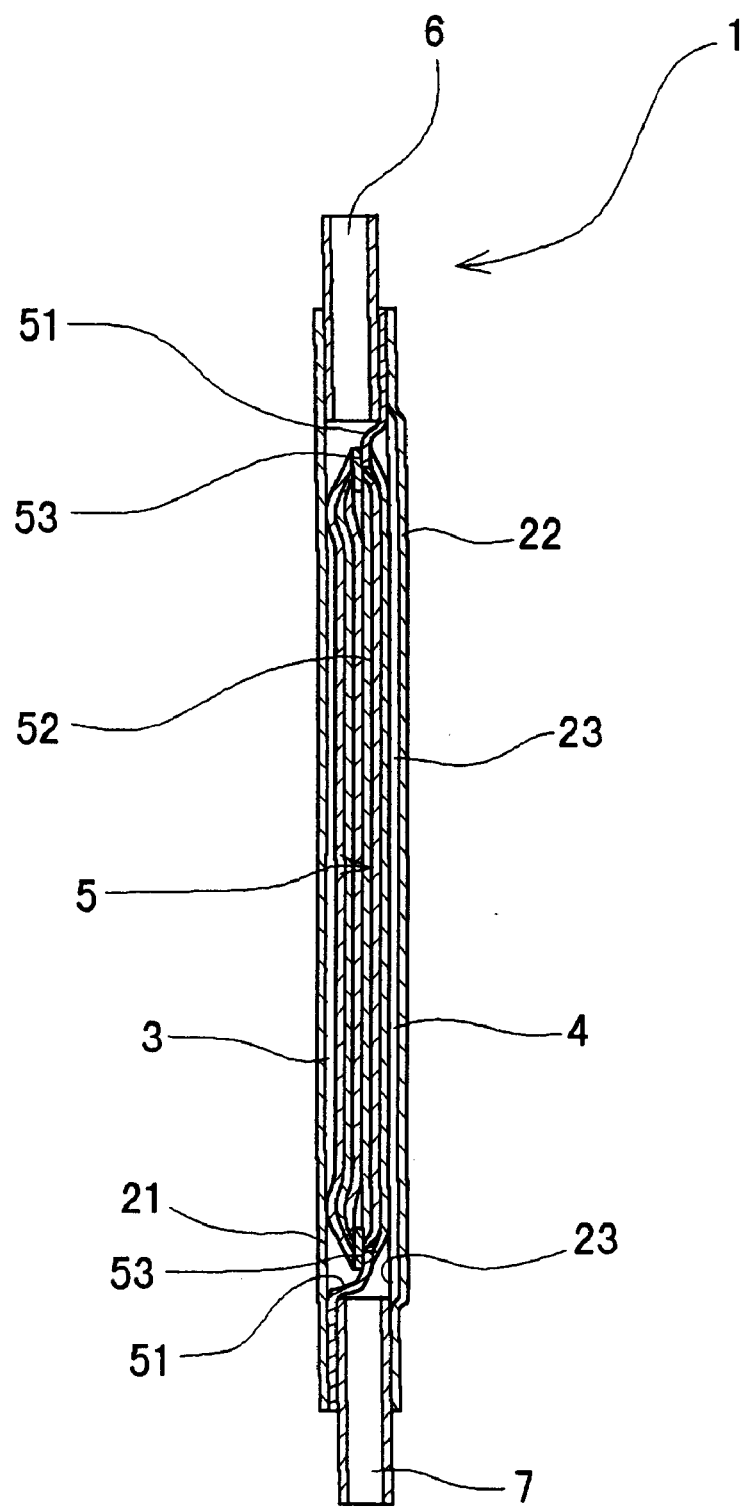
FIG. 4 is an enlarged sectional view showing the white blood cell-removing device of FIG. 1 taken along a line B—B.

As shown in FIGS. 1, 2 and 4, the white blood cell-removing device (leukocyte depleting device) 1 of the present invention has a bag-shaped housing 2 made of soft resin; a white blood cell-removing filter member (leukocyte depleting filter) 5 partitioning the inside of the housing 2 into an inlet side blood chamber 3 and an outlet side blood chamber 4; a blood inlet port 6 positioned at one side of the housing 2 and communicating with the inlet side blood chamber 3; and a blood outlet port 7 positioned at the other side of the housing 2 and communicating with the outlet side blood chamber 4. An unevenness or concave/convex surface having a difference of 0.2–2 mm between its highest and lowest points is formed on an inner surface 2a of the bag-shaped housing 2 made of soft resin and confronting one surface of the white blood cell-removing filter member 5 forming the outlet side blood chamber 4.

Figure 3:
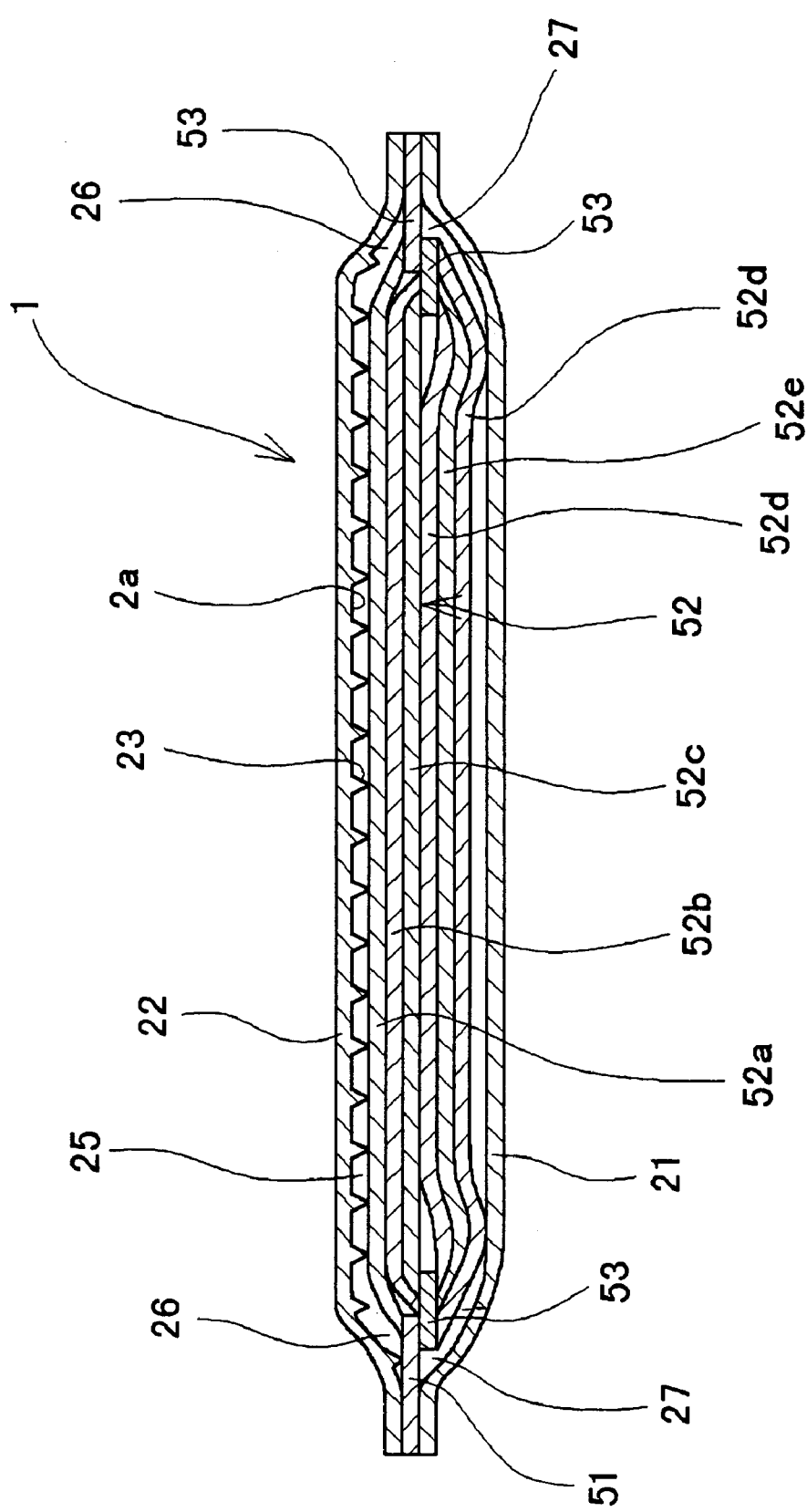
FIG. 3 is an enlarged sectional view showing the white blood cell-removing device of FIG. 1 taken along a line A—A.
Figure 5:
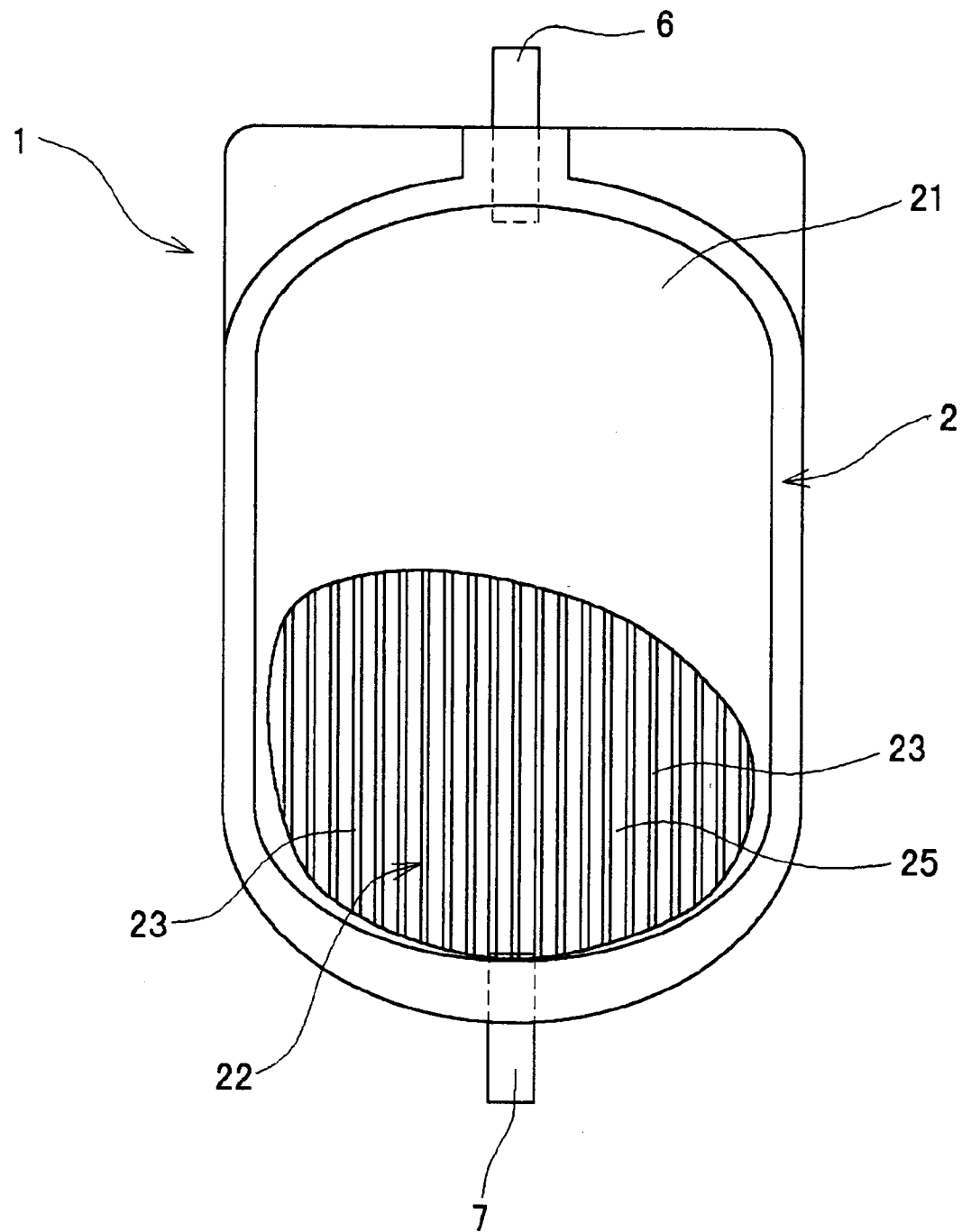
FIG. 5 shows a state in which a part of the white blood cell-removing device of FIG. 1 has been removed therefrom.

As shown in FIGS. 3, 4, and 5, in the white blood cell-removing device 1 of the embodiment, the bag-shaped housing 2 is made of two thermoplastic soft resinous sheets 21 and 22. The resinous sheet 21 is positioned at the side of the inlet side blood chamber 3. The resinous sheet 22 is positioned at the side of the outlet side blood chamber 4. The concave/convex surface having the height of 0.2–2 mm is formed on the inner surface 2a of the resinous sheet 22. In other words, the concave/convex surface is formed on the surface of resinous sheet 22 confronting one surface of the white blood cell-removing filter member 5 forming the outlet side blood chamber 4. The reason the concave/convex (unevenness) surface is formed on the inner surface 2a of the resinous sheet 22 is to prevent the white blood cell-removing filter member 5 and the inner surface 2a of the resinous sheet 22 from contacting closely each other, even in the state in which the white blood cell-removing filter member 5 presses the inner surface 2a of the bag-shaped housing 2 (inner surface 2a of the resinous sheet 22) made of soft resin. That is, the concave/convex surface is formed to securely obtain a blood duct between the white blood cell-removing filter member 5 and the inner surface 2a of the housing 2 (inner surface 2a of the resinous sheet 22) and thereby prevent reduction of a filtering speed.

As shown in FIGS. 1, 3, and 5, in the white blood cell-removing device 1 of the embodiment, a plurality of ribs 23 is formed on the inner surface 2a of the resinous sheet 22 such that the ribs 23 are substantially parallel with one another and extend from one end of the housing 2 to the other end thereof. In other words, the ribs 23 extends from a blood inlet port side to a blood outlet port side blood or flow direction). The ribs 23 have a function of preventing the white blood cell-removing filter member 5 and the inner surface 2a of the resinous sheet 22 from contacting each other closely and guiding filtered blood to the blood outlet port 7.

The interval between the adjacent ribs 23 is preferably 1–5 mm. The ribs 23 are arranged at substantially equal intervals. When the interval between the adjacent ribs 23 is more than 1 mm, it is possible to form a sufficiently large blood duct, which allows a filtering period of time to be short. When the interval between the adjacent ribs 23 is less than 5 mm, the concave portion of the inner surface 2a of the resinous sheet 22 is prevented from contacting the white blood cell-removing filter member 5 closely. Thus, the blood duct can be prevented from being sealed.

The width of each of the ribs 23 is preferably 0.5–1 mm. The height (difference between highest and lowest portions) of the lengthwise rib 23 is favorably 0.2–2 mm and more favorably 0.5–1 mm. The sectional shape of the lengthwise rib 23 is preferably triangular, semi-circle, and the like. That is, it is preferable that the lengthwise rib 23 becomes narrow toward its front end.

The mode of the rib 23 is not limited to the above-described one. For example, the ribs 23 are not necessarily formed at regular intervals. Further, the ribs 23 are not necessarily parallel with one another. Furthermore, the ribs 23 are not necessarily linear but may extend curvedly from one end of the housing 2 to the other end thereof.

Figure 7:
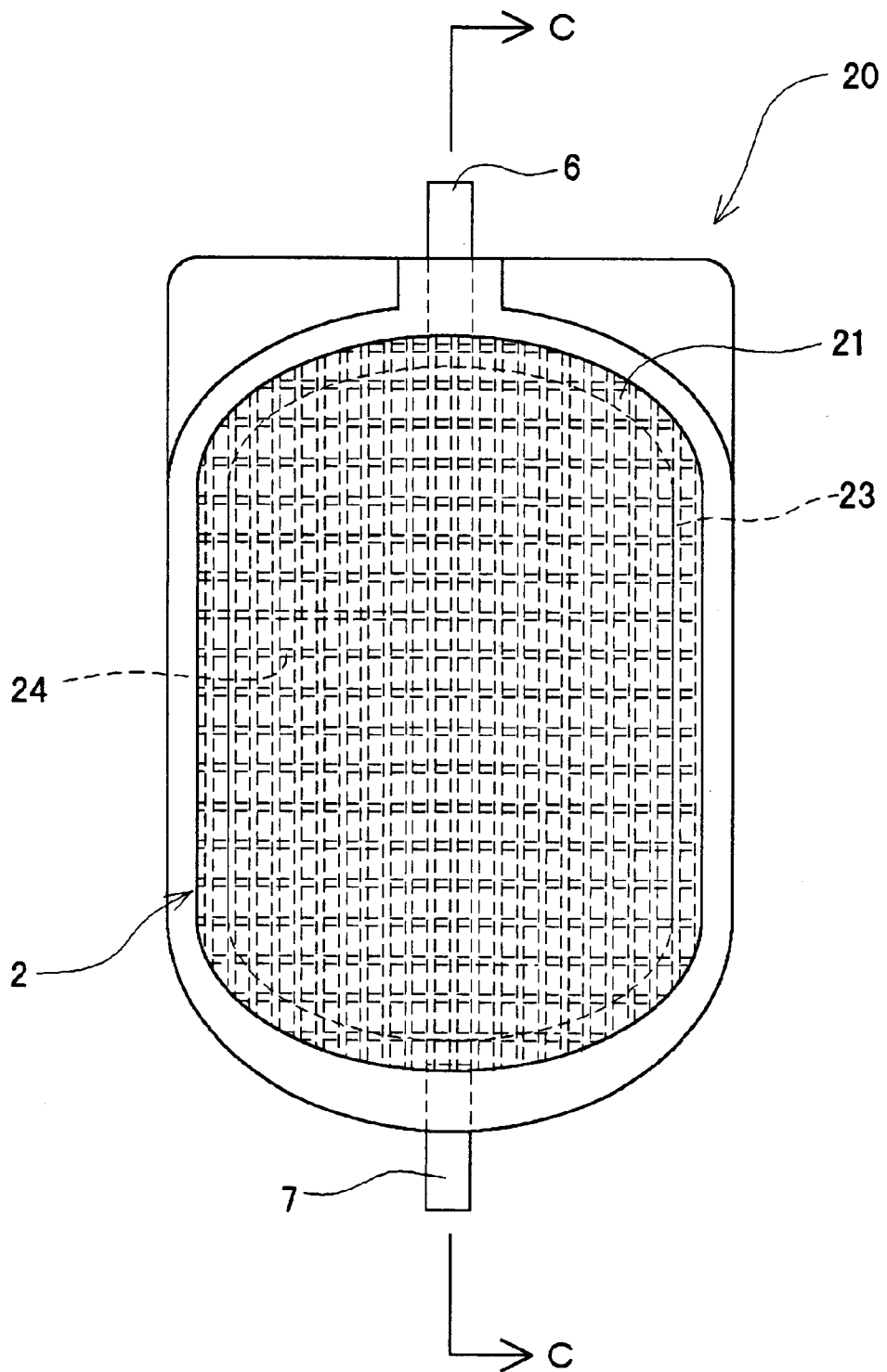
FIG. 7 is a front view showing a white blood cell-removing device of another embodiment of the present invention as viewed from an outlet side blood chamber thereof.
Figure 8:
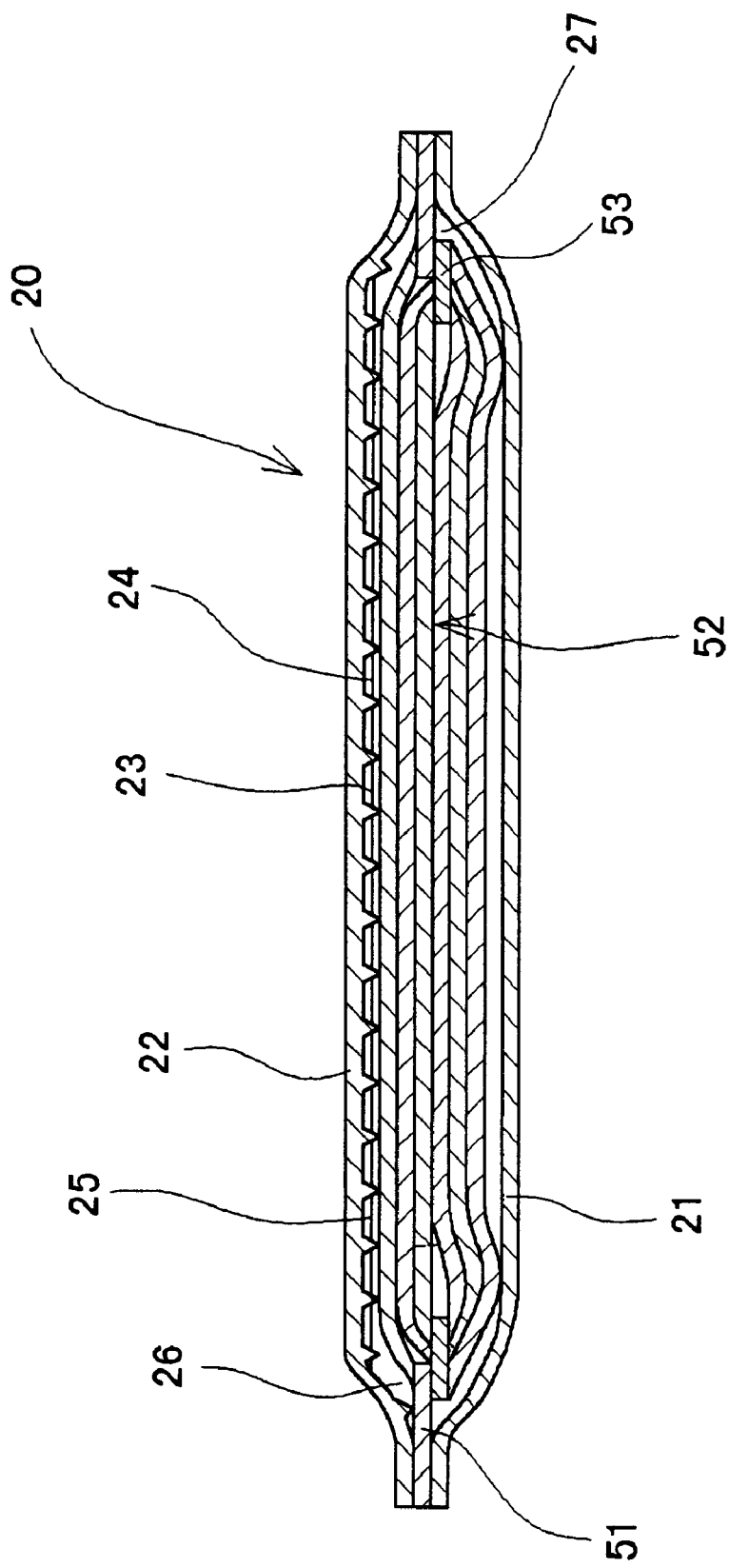
FIG. 8 is an enlarged sectional view showing the white blood cell-removing device of FIG. 7 taken along a line C—C.
Figure 9:
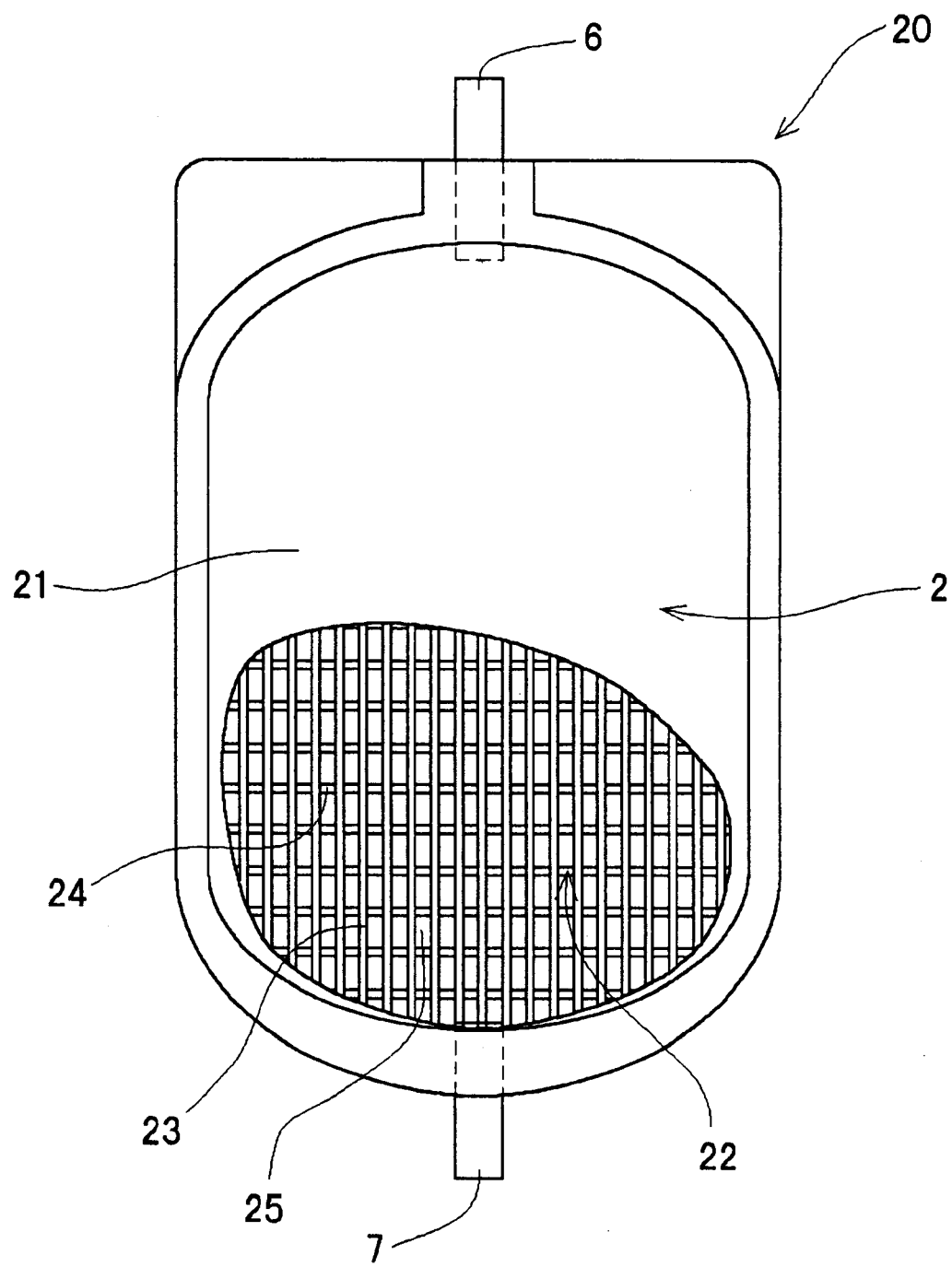
FIG. 9 shows a state in which a part of the white blood cell-removing device of FIG. 7 has been removed therefrom.

Further, as in the case of a white blood cell-removing device 20 of an embodiment shown in FIGS. 7 through 9, a plurality of lengthwise ribs 23 and a plurality of widthwise ribs 24 may be so formed on the inner surface 2a of the resinous sheet 22 that the lengthwise ribs 23 extend from one end of the housing 2 to the other end thereof and the widthwise ribs 24 intersect with the lengthwise ribs 23 substantially perpendicularly thereto. In this case, the interval between the adjacent lengthwise ribs 23 and that between the adjacent widthwise ribs 24 are both preferably 1–5 mm. Preferably, they may be formed at substantially regular intervals. The width of the lengthwise rib 23 and that of the widthwise rib 24 are both preferably 0.5–1 mm. The height (difference between highest and lowest portions) of the lengthwise rib 23 is favorably 0.2–2 mm and more favorably 0.5–1 mm.

The height (difference between highest and lowest portions) of the widthwise rib 24 is favorably 0.2–1 mm and more favorably 0.2–0.5 mm. Favorably, the height of the widthwise rib 24 is smaller than that that of the lengthwise rib 23. More specifically, it is preferable that the height of the widthwise rib 24 is smaller than the lengthwise rib 23 by 0.3 mm–1 mm. Preferably, the interval between the adjacent widthwise ribs 24 is larger than that between the adjacent lengthwise ribs 23. More specifically, it is preferable that the interval between the adjacent widthwise ribs 24 is larger than that between the adjacent lengthwise ribs 23 by 1–2 mm.

Figure 10:
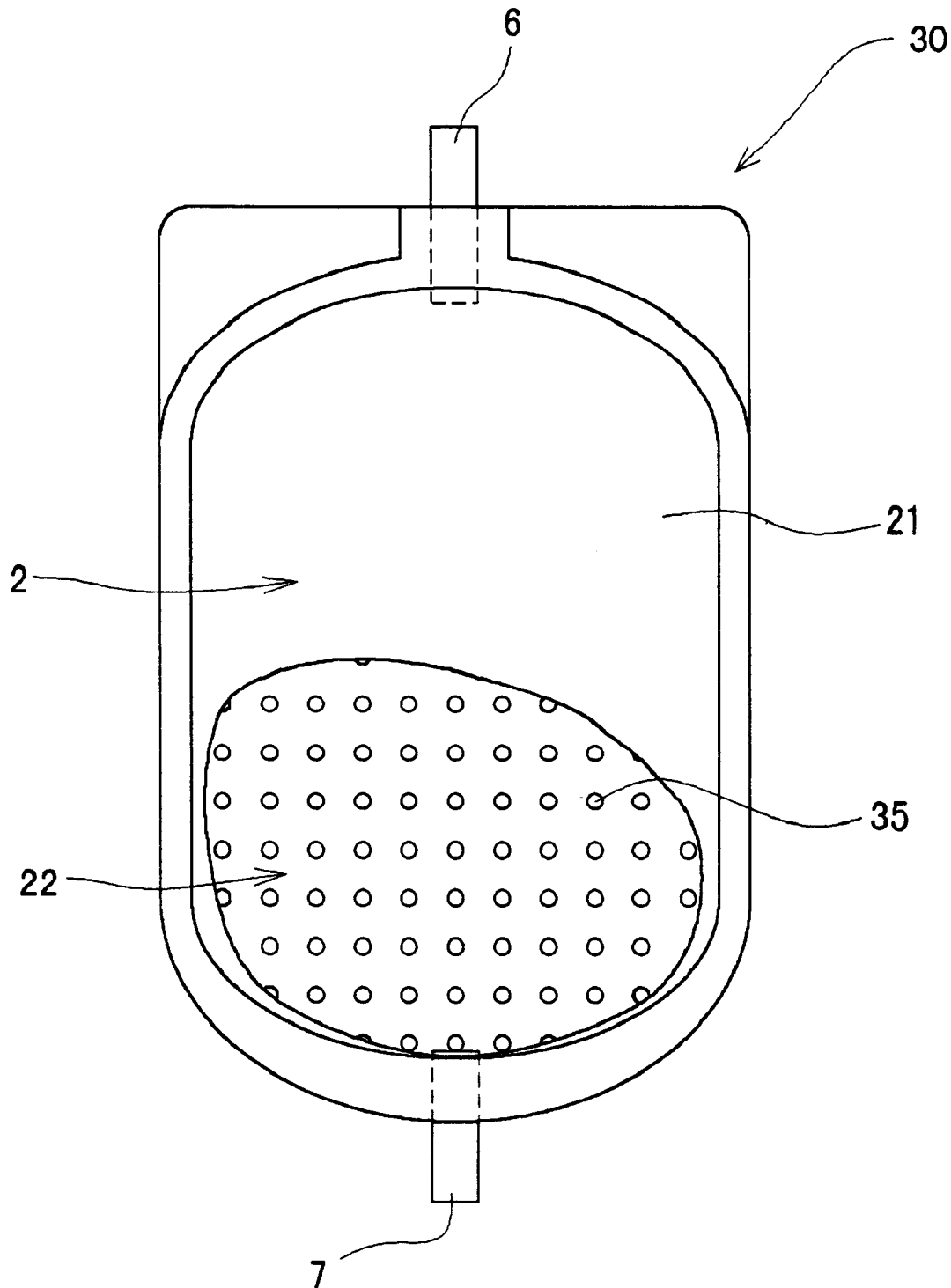
FIG. 10 shows a state in which a part of a white blood cell-removing device of another embodiment of the present invention has been removed therefrom.

The concave/convex surface formed on the inner surface 2a of the bag-shaped housing 2 made of soft resin and confronting one surface of the white blood cell-removing filter member 5 forming the outlet side blood chamber 4 is not necessarily constructed of the above-described rib. For example, as in the case of a white blood cell-removing device 30 of an embodiment shown in FIG. 10, the rib may consist of many projections 35 scattered on the inner surface 2a of the resinous sheet 22. In this case, the height (difference between highest and lowest portions) of the projection 35 is favorably 0.2–2 mm and more favorably 0.5–1 mm. The shape of the projection 35 is favorably conic, polygonal, semi-spherical, and the like. It is most favorable that the projection 35 is semi-spherical. The area of the projection 35 is preferably 0.5–10 mm$^2$. The number of the projections 35 is preferably 3–50 per 1 cm$^2$, although it is varied according to the area of the base of the projection 35. The distance between the adjacent projections 35 is preferably 1–10 mm.

In the white blood cell-removing device 1 of the embodiment, the white blood cell-removing filter member 5 is formed of a sheet-shaped frame 51 made of thermoplastic soft resin and a filtering part 52 whose peripheral portion is directly or indirectly fixed to the sheet-shaped frame 51 made of thermoplastic soft resin. The filtering part 52 is formed of a laminate consisting of a plurality of filtering materials. The white blood cell-removing filter member 5 has a filtering part formed of the filtering part 52 and a non-filtering part formed on the entire periphery of the filtering part 52. The white blood cell-removing filter member 5 is sandwiched between two thermoplastic soft resinous sheets 21 and 22. The peripheral portion of the sheet-shaped frame 51 made of thermoplastic soft resin is thermally fused to the two thermoplastic soft resinous sheets 21 and 22. Thereby, the white blood cell-removing filter member 5 partitions the space (interior of housing 2) surrounded with the two thermoplastic soft resinous sheets 21 and 22 into the inlet side blood chamber 3 and the outlet side blood chamber 4.

The soft resinous tube constructing the blood inlet port 6 is thermally fused to a central portion of one end (upper end) of each of the two thermoplastic soft resinous sheets 21 and 22 such that the soft resinous tube constructing the blood inlet port 6 communicates with the inlet side blood chamber 3. An opening at one end of the soft resinous tube is located inside the inlet side blood chamber 3. Similarly, the soft resinous tube constructing the blood outlet port 7 is thermally fused to a central portion of the other end (lower end) of each of the two thermoplastic soft resinous sheets 21 and 22 such that the soft resinous tube constructing the blood outlet port 7 communicates with the outlet side blood chamber 4. An opening at the other end of the soft resinous tube is located inside the outlet side blood chamber 4.

Figure 6:
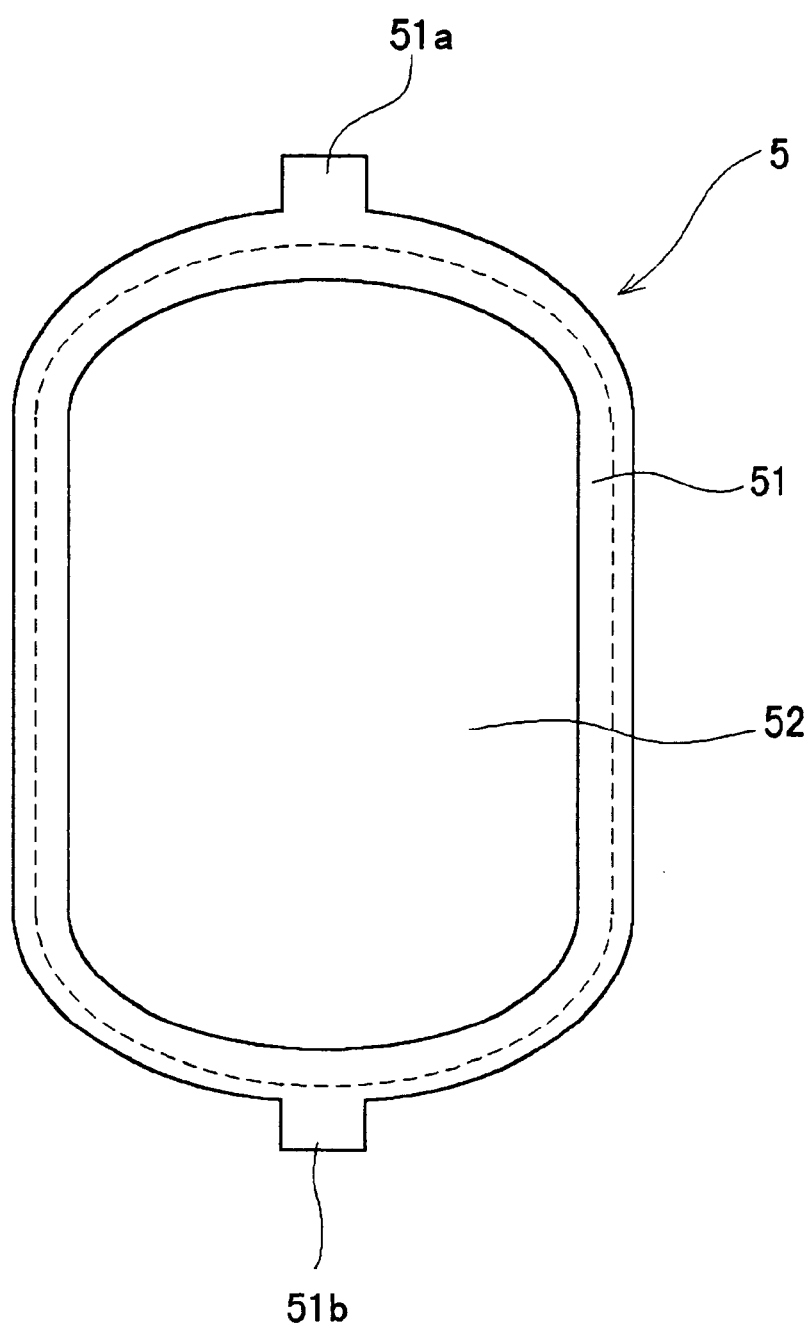
FIG. 6 shows a white blood cell-removing filter member for use in the white blood cell-removing device of the present invention.

As shown in FIG. 6, in the white blood cell-removing device 1 of the embodiment, the sheet-shaped frame 51, made of thermoplastic soft resin, of the white blood cell-removing filter member 5 has short belt-shaped extended portions 51a and 51b projecting outward from a central portion of one end (upper end) thereof and from a central portion of the other end (lower end) thereof, respectively. The soft resinous tube constituting the blood inlet port 6 is fused to the resinous sheets 21 and 22 such that the soft resinous tube is positioned between the extended part 51a and the inlet side resinous sheet 21. The soft resinous tube constituting the blood outlet port 7 is fused to the resinous sheets 21 and 22 such that the soft resinous tube is positioned between the extended part 51b and the outlet side resinous sheet 22. Thereby, the blood inlet port 6 communicates with only the inlet side blood chamber 3, whereas the blood outlet port 7 communicates with only the outlet side blood chamber 4.

The white blood cell-removing filter member 5 is fused to the housing 2 (between the two thermoplastic soft resinous sheets 21 and 22) such that it is located in the region outside the broken line of FIG. 6. Thus, on the peripheral part of the outlet side blood chamber 4, the white blood cell-removing device 1 has a blood duct 26 formed between the part, of the white blood cell-removing filter member 5, which does not contact the filtering part 52 (in other words, the part not having a filtering function, namely, the non-filtering part) and one inner surface of the housing 2. Similarly, on the peripheral part of the inlet side blood chamber 3, the white blood cell-removing device 1 has a blood duct 27 formed between the part, of the white blood cell-removing filter member 5, which does not contact the filtering part 52 (in other words, the part not having a filtering function, namely, the non-filtering part) and the other inner surface of the housing 2.

Because the blood ducts 26 and 27 are formed between the non-filtering parts and the inner surfaces of the housing 2 such that the blood ducts 26 and 27 are located on the inner peripheral part of the housing 2, blood is allowed to flow preferably along the inner peripheral part of the housing 2 and thus prevented from staying thereon. Further, because the blood ducts 26 and 27 are formed in the neighborhood of the blood outlet port 7 inside the outlet side blood chamber 4, processed blood flowing along a duct 25 between the adjacent ribs 23 is preferably guided to the blood outlet port 7. Thus, the construction allows the degree of reduction of the filtering speed to be small. It is preferable that the white blood cell-removing device 1 contains air more than 5 ml.

Flexible thermoplastic resin is used as the material to form the thermoplastic soft resinous sheets 21 and 22 of the housing 2, the sheet-shaped frame 51 of the white blood cell-removing filter member 5, the blood inlet port 6, and the blood outlet port 7. More specifically, the following flexible thermoplastic resins can be used: soft vinyl chloride resin (polyvinyl chloride; a copolymer of vinyl chloride and vinyl acetate; a copolymer of vinyl chloride and ethylene; a copolymer of vinyl chloride and vinylidene chloride; a copolymer of polyvinyl chloride and urethane; a copolymer of polyvinyl chloride and acrylonitrile; a copolymer of vinyl chloride and methyl methacrylate, and a modified substance of soft vinyl chloride resin consisting of any one of the above-described polymers and a plasticizer); a hydrogenated copolymer of styrene, butadiene, and styrene; a thermoplastic elastomer such as a copolymer of styrene, butadiene, and styrene or a hydrogenated substance thereof; a mixture of a thermoplastic elastomer and a softening agent such as polyolefin and ethylene-ethyl acrylate; polyurethane (polyester polyurethane, polyether polyurethane); polyolefin (polyethylene; polypropylene; a copolymer of ethylene and propylene; a copolymer of ethylene and vinyl chloride; a mixture of polypropylene and polyethylene or polybutene); polyester (polyethylene terephthalate; polybutylene terephthalate); and polyamide. The following substances are preferably used: soft vinyl chloride resin; a copolymer of styrene, butadiene, and styrene; polyester; a copolymer of styrene, ethylene, butylene, and styrene; and a thermoplastic elastomer containing one or more of these resins as its main component.

As the material to form the blood inlet port 6 and the blood outlet port 7, hard resin may be used. As the hard resin, hard or semi-hard vinyl chloride, polycarbonate, acrylic resin, styrene resin can be used.

For fixing of the thermoplastic soft resinous sheets 21 and 22 constructing the housing 2; the sheet-shaped frame 51, made of thermoplastic soft resin, of the white blood cell-removing filter member 5; the blood inlet port 6; and the blood outlet port 7, fusing is more favorable than bonding. As fusion welding, an external heating welding by means of heat sealing; and internal welding by means of a high-frequency welder or an ultrasonic welder are used. Welding can be performed by fusing the above-described members simultaneously or in order.

The filtering part 52 of the white blood cell-removing filter member 5 is formed of a laminate or pile up consisting of a plurality of filtering materials each made of a porous material or non-woven cloth. More specifically, six filtering materials 52a, 52b, 52c, 52d, 52e, and 52f are laminated one upon another. Preferably, the number of filtering materials to be laminated one upon another is 2–10. In the embodiment, because many filtering materials are laminated one upon another, some filtering materials (for example, 3–5 materials) are fused to a fusing auxiliary sheet-shaped frame 53. The peripheral portion of the outer side of the fusing auxiliary sheet-shaped frame 53 to which the filtering materials have been fused is fused to the inner peripheral portion of the sheet-shaped frame 51 made of thermoplastic soft resin. As the material of the fusing auxiliary sheet-shaped frame 53, the above-described flexible thermoplastic resin can be used.

The porous material for use in the filtering part 52 means a material having many pores formed in penetration through it in its thickness direction and thus allowing a liquid to permeate therethrough. The following porous materials can be used for the filtering part 52: Natural, synthetic, semi-synthetic, regenerated organic or inorganic fibers; organic or inorganic sponge foam and the like; materials whose pores are formed by elution, sintering, drawing, perforation of pore components; and materials formed by filling organic or inorganic fine particles or fine pieces into a material or connecting them with one another.

As the porous material of the filtering member (filtering material) 52 of the white blood cell-removing filter member 5, a sponge-shaped polyurethane porous material and a polyvinyl formal porous material are selected from the above-described porous materials. In the case of a porous material whose pore has a large diameter, it is preferable to use a thick one. In the case of a thin porous material whose pore has a large diameter, it is preferable to use a plurality thereof by laminating them one upon another. In the case of a porous material having small-diameter pores, a thin one can be used. By appropriately selecting a diameter and a thickness, it is possible to use any kind of porous materials that allow blood cells to pass therethrough. A porous material having interstices whose average diameter is 5–20 $\mu$m is most effective for removing white blood cells.

The diameter of a fiber of the nonwoven cloth for use in the filtering part 52 (filtering material) of the white blood cell-removing filter member 5 is preferably 0.3–20 $\mu$m. As the kind of fibers of the nonwoven cloth, synthetic fibers, semi-synthetic fibers such as regenerated cellulose, natural fibers such as cotton, and inorganic fibers are used. Above all, the synthetic fibers can be preferably used. For example, polyester fibers such as polyethylene terephthalate, nylon, polypropylene, polyacrylonitrile, and the like can be preferably used. As the coating material for the filtering material (nonwoven cloth), the following substances can be used: High polymer materials having hydroxyl group such as hydroxyethyl acrylate, hydroxyethyl methacrylate; high polymer materials having basic functional group containing nitrogen such as a copolymer of diethyl aminoethyl (metha) acrylate and hydroxyethyl (metha) acrylate; polyether urethane. It is possible to coat the surface of the nonwoven cloth with a hydrophilic high polymer or anti-thrombus to allow platelets to favorably permeate the nonwoven cloth.

EXAMPLE

Example 1

The examples of the white blood cell-removing device of the present invention will be described below.

As a material to form the housing, a soft polyvinyl chloride sheet having a length of 110 mm, a width of 75 mm, and a thickness of 0.4 mm and a embossed surface was positioned at the blood inlet side of the housing. Another soft polyvinyl chloride sheet having a length of 110 mm, a width of 75 mm, and a thickness of 0.5 mm was positioned at he blood outlet side of the housing, with sectionally approximately triangular ribs each having a height of 0.8 mm and a base width of 1 mm formed at regular intervals of 2 mm on one surface thereof.

A tube (length: 23 mm, outer diameter: 6 mm) made of a soft polyvinyl chloride sheet was used to form the blood inlet port and the blood outlet port.

As the white blood cell-removing filtering material, six polyurethane porous materials (thickness: 1 mm, average pore diameter: 5 $\mu$m, length: about 85 mm, width: about 65 mm) were used. Five of the six polyurethane porous materials were fused to a fusing auxiliary sheet-shaped frame. One of the six polyurethane porous material and the auxiliary sheet-shaped frame fused five polyurethane porous materials were fused to a fusing sheet-shaped frame (length: 110 mm, width: 75 mm, frame width: 10–25 mm) by heat seal.

A white blood cell-removing filter member formed of the filtering material fused to the fusing auxiliary sheet-shaped frame was placed on the soft polyvinyl chloride sheet positioned at the blood inlet side of the housing. The tube made of the soft polyvinyl chloride sheet was placed between an extended part of the upper side sheet-shaped frame of the white blood cell-removing filter member and the soft polyvinyl chloride sheet positioned at the blood inlet side of the housing. Then, the soft polyvinyl chloride sheet positioned at the blood outlet side of the housing was placed on the white blood cell-removing filter member such that the rib-formed surface of the soft polyvinyl chloride sheet was located over the surface of the white blood cell-removing filter member. Then, the tube made of the soft polyvinyl chloride sheet was placed between an extended part of the lower side sheet-shaped frame of the white blood cell-removing filter member and the soft polyvinyl chloride sheet positioned at the blood outlet side of the housing. Both tubes and the peripheral portion of the sheet-shaped frame of the white blood cell-removing filter member were thermally fused to both soft polyvinyl chloride sheets by a high-frequency welder to prepare a white blood cell-removing device of the present invention.

The sheet-shaped frame has an unfused portion having a length of 3 mm to form an annular portion not having a filtering function on the periphery of the inside (inlet side blood chamber and outlet side blood chamber) of the white blood cell-removing device.

Example 2

A white blood cell-removing device of the present invention was prepared in a manner similar to that of the first example except that ribs approximately triangular in section each and having a height of 0.22 mm and a base width of 1 mm were formed at regular intervals of 2 mm on one surface of the soft polyvinyl chloride sheet having a length of 110 mm, a width of 75 mm, and a thickness of 0.5 mm and positioned at the blood outlet side of the housing.

Example 3

A white blood cell-removing device of the present invention was prepared in a manner similar to that of the first example except that 25 projections (par 1 cm$^2$) each having a height of 0.8 mm and a base area of 1 mm$^2$ were formed at intervals of 2 mm on one surface of the soft polyvinyl chloride sheet having a length of 110 mm, a width of 75 mm, and a thickness of 0.5 mm and positioned at the blood outlet side of the housing.

Example 4

A white blood cell-removing device of the present invention was prepared in a manner similar to that of the first example except that ribs approximately triangular in section each having a height of 0.8 mm and a base width of 1 mm were formed at regular intervals of 5 mm on one surface of the soft polyvinyl chloride sheet having a length of 110 mm, a width of 75 mm, and a thickness of 0.5 mm and positioned at the blood outlet side of the housing.

Example 5

A white blood cell-removing device of the present invention was prepared in a manner similar to that of the first example except that ribs approximately triangular in section each having a height of 2.0 mm and a base width of 1.5 mm were formed at regular intervals of 2 mm on one surface of the soft polyvinyl chloride sheet having a length of 110 mm, a width of 75 mm, and a thickness of 0.5 mm and positioned at the blood outlet side of the housing.

Comparison Example 1

A white blood cell-removing device of the present invention was prepared in a manner similar to that of the first example except that ribs approximately triangular in section each having a height of 0.18 mm and a base width of 1 mm were formed substantially at regular intervals of 2 mm on one surface of the soft polyvinyl chloride sheet having the length of 110 mm, the width of 75 mm, and the thickness of 0.5 mm and positioned at the blood outlet side of the housing.

Comparison Example 2

A white blood cell-removing device of the present invention was prepared in a manner similar to that of the first example except that ribs approximately triangular in section each having a height of 2.5 mm and a base width of 1.5 mm were formed substantially at regular intervals of 2 mm on one surface of the soft polyvinyl chloride sheet having a length of 110 mm, a width of 75 mm, and a thickness of 0.5 mm and positioned at the blood outlet side of the housing.

Comparison Example 3

A white blood cell-removing device of the present invention was prepared in a manner similar to that of the first example except that the same soft polyvinyl chloride sheet was used on the blood-inlet and outlet sides of the housing; a polyester nonwoven cloth was interposed between the soft polyvinyl chloride sheet at the blood outlet side and the white blood cell-removing filter member; and the peripheral portion of the nonwoven cloth was fused to the soft polyvinyl chloride sheets at the blood inlet side and that at the blood outlet side.

Comparison Example 4

A white blood cell-removing device of the present invention was prepared in a manner similar to that of the first example except that the same soft polyvinyl chloride sheet was used on the blood inlet and outlet sides of the housing; two tubes (length: 85 mm, outer diameter: 4.4 mm, inner diameter: 3.0 mm) made of soft polyvinyl chloride was sandwiched between the soft polyvinyl chloride sheets at the blood outlet side and the white blood cell-removing filter member such that the two tubes were approximately parallel with a blood flow direction; and in fusing the white blood cell-removing filter member to the upper and lower (blood outlet and inlet sides) soft polyvinyl chloride sheets by a high-frequency welder, the two tubes were also fused to the soft polyvinyl chloride sheets.

Experiment

Using the white blood cell-removing devices of the embodiments and the white blood cell-removing devices of the comparison examples, the following experiments were conducted.

Using a triple bag containing an ACD liquid and a MAP liquid, 400 ml of blood was collected. The blood was centrifuged in 18 hours after the blood collection was performed. Blood plasma obtained as a supernatant liquid was put in a transfer bag. Then, the MPA liquid was added to thick red blood cell left in a blood collection bag (donor bag) to obtain MPA-added thick red blood cells. Himac CR7 (Nissei Sangyo Co., Ltd.) was used for the centrifuge. The centrifuge was carried out in the condition of 22° C., 4100 rpm, and seven minutes.

Using a tube sealer, unrequired bags and tubes were cut off to obtain a bag containing the MPA-added thick red blood cell. After the MPA-added thick red blood cell was kept at 4° C. for three days, a white blood cell-removing device was connected with the bag to collect white blood cell-removed thick red blood cells. In collecting the white blood cell-removed thick red blood cells, the bag containing the MPA-added thick red blood cells was placed at a higher position, and a bag for collecting the white blood cell-removed thick red blood cells was placed on an electronic balance placed about 1 m downward from the bag containing the MPA-added thick red blood cells. The white blood cell-removing device was placed at a location intermediate between both bags to collect the white blood cell-removed thick red blood cells by utilizing the vertical difference in the positions thereof.

Measurements were made on the period of time for collecting the white blood cell-removed thick red blood cells, the weight of the collected white blood cell-removed thick red blood cells, the number of platelets of the collected white blood cell-removed thick red blood cells, and the number of remaining white blood cells of the collected white blood cell-removed thick red blood cells. As the electronic balance (measurement of weight), BL-3200S manufactured by Shimazu Seisakusho Co., Ltd. was used. As the measuring apparatus, Sysmex NE-6000 manufactured by Toa Iyo Denshi Co., Ltd. was used to measure the number of blood cells and that of platelets. Nageotte method was used to measure a slight amount of white blood cells.

The result is as shown in tables 1 through 3. Five data was used for each of the measured items. The number of red blood cells, that of platelets, and that of white blood cells shown in the tables 1 through 3 are values converted from measured values supposing that they were present.

Reference symbols ⊚, ○, Δ, and X in the tables 1 through 3 indicate that evaluation is very favorable, favorable, a permissible range, and unfavorable, respectively.

TABLE 1

|  | Ex. 1 | Ex. 2 | Ex. 3 |
|---|---|---|---|
| Before filtration |  |  |  |
| Liquid amount (ml) | 345 ± 12 | 350 ± 13 | 343 ± 11 |
| Number of red blood cells (×10$^{10}$) | 210 ± 19 | 212 ± 20 | 209 ± 21 |
| Number of platelets (×10$^9$) | 106 ± 9 | 98 ± 13 | 121 ± 11 |
| Number of white blood cells (×0$^7$) | 227 ± 22 | 265 ± 25 | 210 ± 28 |
| After filtration |  |  |  |
| Liquid amount (ml) | 317 ± 11 | 322 ± 12 | 316 ± 9 |
| Number of red blood cells (×10$^{10}$) | 193 ± 19 | 195 ± 20 | 192 ± 21 |
| Number of platelets (×10$^9$) | 10 ± 2 | 12 ± 3 | 9 ± 3 |
| Number of white blood cells (×10$^4$) | 5 ± 2 | 5 ± 3 | 5 ± 3 |
| Filtering time (min) | 10 ± 2 | 11 ± 3 | 18 ± 3 |
| Evaluation |  |  |  |
| Collection percentage of red blood cell | ○ | ○ | ○ |
| Removal percentage of white blood cell | ○ | ○ | ○ |
| Filtering time | ⊚ | ⊚ | Δ |
| Productivity & cost | ○ | ○ | ○ |

TABLE 2

|  | Ex. 4 | Ex. 5 |
|---|---|---|
| Before filtration |  |  |
| Liquid amount (ml) | 347 ± 12 | 350 ± 13 |
| Number of red blood cells (×10$^{10}$) | 211 ± 19 | 211 ± 20 |
| Number of platelets (×10$^9$) | 107 ± 9 | 98 ± 13 |
| Number of white blood cells (×10$^7$) | 226 ± 22 | 261 ± 25 |
| After filtration |  |  |
| Liquid amount (ml) | 318 ± 11 | 324 ± 12 |
| Number of red blood cells (×10$^{10}$) | 198 ± 19 | 196 ± 20 |

TABLE 2-continued

|  | Ex. 4 | Ex. 5 |
|---|---|---|
| Number of platelets (×10$^9$) | 11 ± 2 | 12 ± 2 |
| Number of white blood cells (×10$^4$) | 5 ± 2 | 5 ± 3 |
| Filtering time (min) | 13 ± 2 | 15 ± 5 |
| Evaluation |  |  |
| Collection percentage of red blood cell | ○ | ○ |
| Removal percentage of white blood cell | ○ | ○ |
| Filtering time | ⊚ | ○ |
| Productivity & cost | ○ | ○ |

TABLE 3

|  | Co. ex. 1 | Co. ex. 2 | Co. ex. 3 | Co. ex. 4 |
|---|---|---|---|---|
| Before filtration |  |  |  |  |
| Liquid amount (ml) | 351 ± 16 | 350 ± 13 | 344 ± 11 | 348 ± 13 |
| Number of red blood cells (×10$^{10}$) | 213 ± 20 | 212 ± 19 | 213 ± 18 | 211 ± 20 |
| Number of platelets (×10$^9$) | 102 ± 10 | 107 ± 9 | 102 ± 11 | 101 ± 13 |
| Number of white blood cells (×10$^7$) | 225 ± 19 | 264 ± 31 | 231 ± 19 | 251 ± 23 |
| After filtration |  |  |  |  |
| Liquid amount (ml) | 323 ± 16 | 314 ± 11 | 316 ± 9 | 320 ± 10 |
| Number of red blood cells (×10$^{10}$) | 196 ± 20 | 189 ± 19 | 198 ± 18 | 194 ± 20 |
| Number of platelets (×10$^9$) | 10 ± 3 | 9 ± 3 | 8 ± 2 | 10 ± 3 |
| Number of white blood cells (×10$^4$) | 5 ± 3 | 5 ± 3 | 5 ± 3 | 5 ± 3 |
| Filtering time (min) | 25 ± 5 | 12 ± 2 | 20 ± 10 | 55 ± 15 |
| Evaluation |  |  |  |  |
| Collection percentage of blood cell | ○ | X | ○ | ○ |
| Removal percentage of white blood cell | ○ | ○ | ○ | ○ |
| Filtering time | X | ⊚ | Δ | X |
| Productivity & cost | ○ | ○ | X | X |

In the first comparison example, because the difference between the highest and lowest portions of the rib was small, a sufficient flow speed could not be obtained and thus the filtering period of time took long. In comparison example 2, the difference between the highest and lowest portions of the rib was so large that much blood remained in the dead space. Thus, red blood cell was collected at a low percentage (less than 90%). When the convex portion of the rib is thick, there is much possibility of unfavorable sealing in forming a bag-shaped housing.

The third comparison example has a problem the non-woven cloth is expensive, a problem of poor productivity, i.e., much time and labor is required to insert it between the soft polyvinyl chloride sheet and the white blood cell-removing filter member, and a problem that there is a possibility of unfavorable sealing. Similarly to the third comparison example, the fourth comparison example has a problem that the white blood cell-removing device is expensive, a problem of poor productivity, and a problem that a necessary gap cannot be formed. Thus, according to the fourth comparison example, the filtering period of time took long.

The first embodiment of the white blood cell-removing apparatus of the present invention will be described below, using FIG. 11.

A white blood cell-removing apparatus 100 of the first embodiment includes a white blood cell-removing device 101 comprising a housing made of soft resin; a white blood cell-removing member partitioning the inside of the housing into an inlet side blood chamber and an outlet side blood chamber, a blood inlet port 106 positioned at one side of the housing and communicating with the inlet side blood chamber and a blood outlet port 107 positioned at the other side of the housing and communicating with the outlet side blood chamber; a first tube 111 whose one end is provided with a connection portion 108 to be connected with a unprocessed blood filling container and whose other end is connected with the blood inlet port 106; a processed blood collection container 110 made of soft resin; and a second tube 112 connecting the processed blood collection container 110 and the blood outlet port 107 with each other. The processed blood collection container 110 contains air whose amount is equal to or more than the difference between the volume of blood filled in the outlet side blood chamber of the white blood cell-removing device 101 and the volume of air preserved therein.

The second embodiment of the white blood cell-removing apparatus of the present invention will be described below by using FIG. 12.

A white blood cell-removing apparatus 120 of the embodiment includes a white blood cell-removing device 101 a housing made of soft resin; a white blood cell-removing member partitioning the inside of the housing into an inlet side blood chamber and an outlet side blood chamber, a blood inlet port 106 positioned at one side of the housing and communicating with the inlet side blood chamber and a blood outlet port 107 positioned at the other side of the housing and communicating with the outlet side blood chamber; an unprocessed blood filling container 109 made of soft resin; a first tube 111 connecting the unprocessed blood filling container 109 made of soft resin and the blood inlet port 106 with each other; a processed blood collection container 110 made of soft resin; and a second tube 112 connecting the processed blood collection container 110 and the blood outlet port 107 with each other. The processed blood collection container 110 contains air whose amount is equal to or more than the difference between the volume of blood filled in the outlet side blood chamber of the white blood cell-removing device 101 and the volume of air preserved therein.

The difference between the white blood cell-removing apparatus 100 and 120 is that the unprocessed blood filling container 109 is provided for the white blood cell-removing apparatus 120 and the connection portion 108 is provided for the white blood cell-removing apparatus 100. In other parts, the white blood cell-removing apparatuses 100 and 120 have the same construction. Each of the white blood cell-removing apparatuses 100 and 120 has a clamp 121 serving as a first duct opening/closing member and installed on the first tube 111 and a clamp 122 serving as a second duct opening/closing member and installed on the second tube 112.

It is preferable that each of the white blood cell-removing apparatuses 100 and 120 has a flow-out restraining part for restraining air filled in the processed blood collection container 110 from flowing out from the white blood cell-removing apparatuses 100 and 120. The flow-out restraining part having the above function can be formed by closing the first duct opening/closing member 121 or the second duct opening/closing member 122. The flow-out restraining part may be also formed by providing a breakable duct regulation member on the first tube 111, the second tube 112 or at the portion where the second tube 112 and the processed blood collection container 110 are connected with each other. In the white blood cell-removing apparatuses 100 and 120 of the embodiment, a breakable duct regulation member 105 is provided on the second tube 112 and at the portion where the second tube 112 and the processed blood collection container 110 are connected with each other to prevent air filled in the processed blood collection container 110 from flowing out from the white blood cell-removing apparatuses 100 and 120 during transport thereof. The breakable duct regulation member 105 prevents circulation of air in a normal state and allows communication of air between the second tube 112 and the processed blood collection container 110 when it is broken by applying an external force thereto.

As the white blood cell-removing device 101, the white blood cell-removing device having the housing made of soft resin can be preferably used.

As the material of the unprocessed blood filling container 109 and the processed blood collection container 110, soft synthetic resins heat-resistant to some extent are used by processing them into a bag shape: polyolefin or a polyolefin partial cross-linked substance (for example, polyethylene, polypropylene, a copolymer of ethylene and propylene, a mixture of polypropylene and polyethylene or polybutene), a copolymer of ethylene and vinyl acetate (EVA), polyester (polyethylene terephthalate, polybutylene terephthalate), and soft polyvinyl chloride. The container 109 and 110 may be formed by blow-molding any one of the above-described resins, by welding peripheral portions of two sheets made of any one of the above-described resins or by welding peripheral portions of an opening of a cylindrical material formed by extrusion molding of any one of the above-described resins. As the material of the first and second tubes 111 and 112, the above-described soft synthetic resins are used.

As the clamps 121 and 122, a slide clamp, a roller clamp, and a one-touch clamp can be used.

Air is filled in the processed blood collection container 110 such that the amount thereof is equal to or more than the difference between the volume of blood to be filled in the outlet side blood chamber of the white blood cell-removing device 101 and the volume of air to be preserved therein. Because the housing of the white blood cell-removing device 101 is made of soft resin, there is a possibility that a difference is generated between the volume of air preserved in the outlet side blood chamber of the white blood cell-removing device 101 and the volume of blood filled therein. The air filled in the processed blood collection container 110 is effective for collecting processed blood reliably as described below.

That is, in the white blood cell-removing device composed of the soft resin, a difference often occurs between the volume of air preserved in the outlet side blood chamber thereof and the volume of blood filled therein. The supplement amount of air in the outlet side blood chamber of the white blood cell-removing device 101 is about 5 ml. When blood is filled therein, the supplement amount of air therein may become about 20 ml owing to expansion of the housing of the white blood cell-removing device 101. In this case, it is impossible to collect about 15 ml of processed blood only by utilization of the air in the white blood cell-removing device 101. It is possible to securely collect the processed blood by filling air into the processed blood collection container 110 in advance such that the amount of the air is equal to or more than the difference between the volume of blood to be filled in the outlet side blood chamber of the white blood cell-removing device 101 and the volume of air to be preserved therein.

It is preferable to fill air into the processed blood collection container 110 such that the amount thereof is more than the volume of the outlet side blood chamber of the white blood cell-removing device 101. It is also preferable to fill air into the processed blood collection container 110 such that the amount thereof is more than the sum of the volume of the outlet side blood chamber of the white blood cell-removing device 101 and the volume of the second tube 112. Preferably, the amount of air to be filled into the processed blood collection container 110 is 15–40 ml although it is different depending on the volume of the outlet side blood chamber of the white blood cell-removing device 101.

The operation of the white blood cell-removing apparatus having the processed blood collection container 110 in which air has been filled will be described below by using the embodiment shown in FIGS. 11 and 12.

Figure 13:
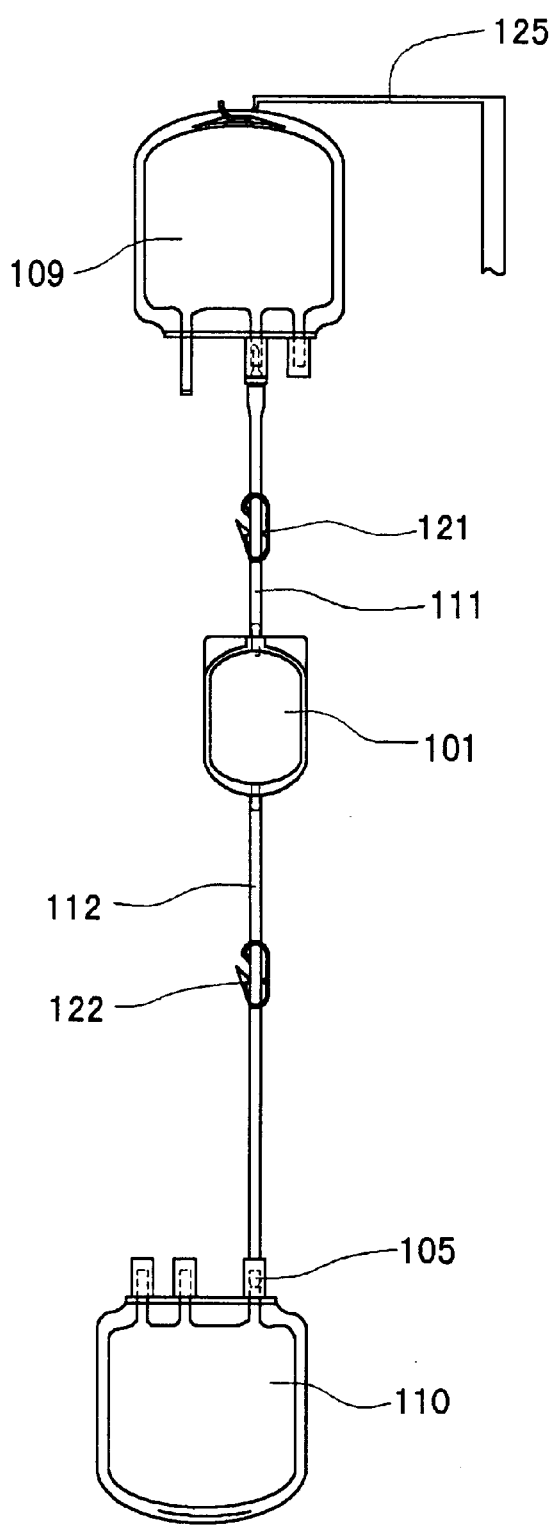
FIG. 13 is an explanatory view showing a white blood cell-removing method of the present invention.

Initially, the clamp 121 installed on the first tube 111 and the clamp 122 installed on the second tube 112 are closed. Then, the connection portion 108 is pierced into a discharge opening of the unprocessed blood filling container 109. As shown in FIG. 13, the unprocessed blood filling container 109 is hung on a stand 125. Then, the clamp 122 is opened and the duct regulation member 105 is broken. Then, turning the white blood cell-removing device 101 upside down, the clamp 121 is opened. As a result, an initial flow of blood is introduced into the white blood cell-removing device 101. As a result, air in the white blood cell-removing device 101 is expelled and introduced into the processed blood collection container 110. After the air in the white blood cell-removing device 101 is expelled, and the interior thereof is filled with blood, the white blood cell-removing device 101 is turned downside up, as shown in FIG. 13, to perform a white blood cell-removing operation.

After the white blood cell-removing operation terminates, air (air introduced into the processed blood collection container 110 by the above operation and air filled therein in advance) contained in the processed blood collection container 110 is moved toward the second tube 112 to press the processed blood collection container 110. Consequently, the outlet side blood chamber of the white blood cell-removing device 101 expands, and thus air and a part of processed blood flow thereinto. When the pressing of the processed blood collection container 110 terminates, blood staying in the outlet side blood chamber of the white blood cell-removing device 101 and in the second tube 112 flow downward. As a result, air remains in the outlet side blood chamber of the white blood cell-removing device 101. Thereby, it is possible to increase the collection amount of blood. Preferably, the operation is performed with the clamp 121 sealed.

The first embodiment of the white blood cell-removing method of the present invention will be described below.

The white blood cell-removing method is carried out by using a white blood cell-removing apparatus comprising a white blood cell-removing device having a bag-shaped housing made of soft resin; a white blood cell-removing member partitioning an inside of the housing into an inlet side blood chamber and an outlet side blood chamber; a blood inlet port positioned at one side of the housing and communicating with the inlet side blood chamber; and a blood outlet port positioned at the other side of the housing and communicating with the outlet side blood chamber. The white blood cell-removing method is carried out in a state where an unprocessed blood filling container made of soft resin and containing unprocessed blood is connected with the white blood cell-removing device at a blood flow inlet side thereof through a first tube, and a processed blood collection container made of soft resin and collecting treated blood is connected with the white blood cell-removing device at a blood flow outlet side thereof through a second tube. The method comprises the steps of pressing the white blood cell-removing device, with a blood outlet side (blood outlet port or tube connecting white blood cell-removing device and processed blood collection container with each other) of the white blood cell-removing device closed; feeding at least one part of air inside the white blood cell-removing device to the unprocessed blood filling container; introducing the blood contained in the unprocessed blood filling container into the white blood cell-removing device; feeding the air inside the white blood cell-removing device to the processed blood collection container (before processed blood flows into the processed blood collection container); feeding the blood inside the unprocessed blood filling container to the processed blood collection container by passing the blood through the white blood cell-removing device; feeding the air inside the processed blood collection container to the outlet side blood chamber of the white blood cell-removing device or to the second tube or to the outlet side blood chamber and the second by pressing the processed blood collection container; and collecting processed blood in the outlet side blood chamber of the white blood cell-removing device or processed blood in the second tube or processed blood in the outlet side blood chamber and the second tube into the processed blood collection container.

Figure 11:
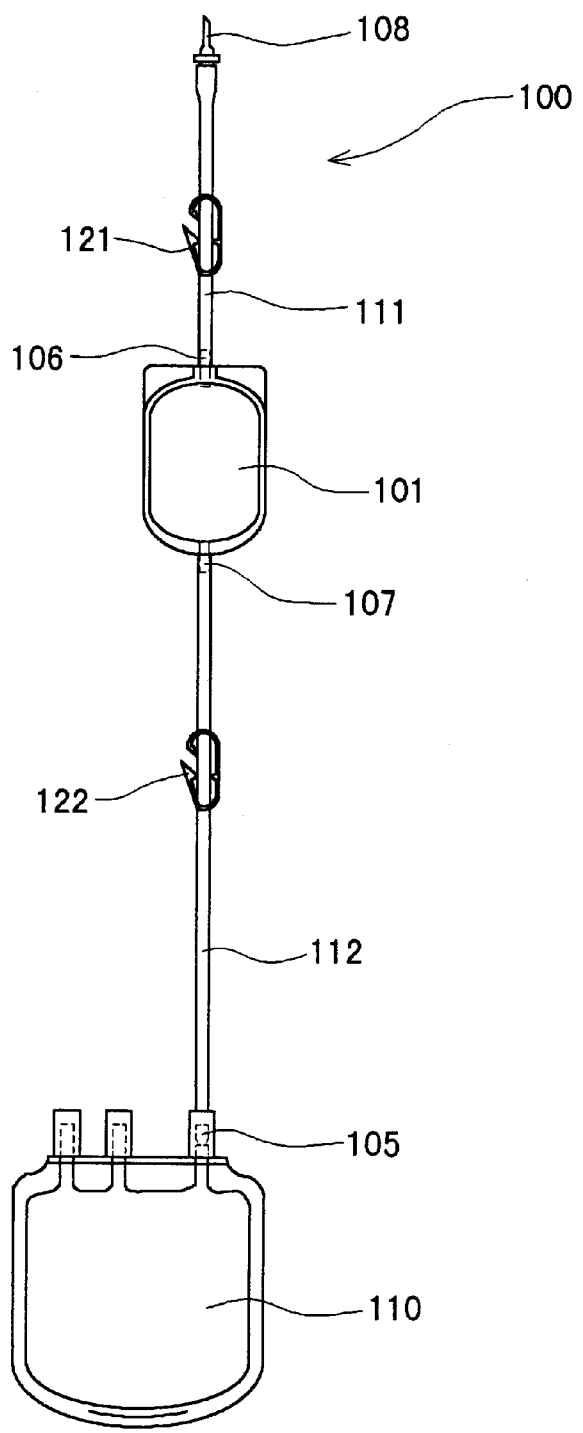
FIG. 11 is an explanatory view showing a white blood cell-removing apparatus of an embodiment of the present invention.

In the white blood cell-removing method, the white blood cell-removing apparatus 100 shown in FIG. 11 is used. The white blood cell-removing method is described below, supposing that the white blood cell-removing apparatus 100 is not provided with the duct regulation member 105.

The white blood cell-removing apparatus 100 includes the white blood cell-removing device 101 comprising the housing made of soft resin; the white blood cell-removing member partitioning the inside of the housing into the inlet side blood chamber and the outlet side blood chamber, the blood inlet port 106 positioned at one side of the housing and communicating with the inlet side blood chamber and the blood outlet port 107 positioned at the other side of the housing and communicating with the outlet side blood chamber; the first tube 111 whose one end is provided with the connection portion 108 to be connected with the unprocessed blood filling-container and whose other end is connected with the blood inlet port 106; the processed blood collection container 110 made of soft resin; the second tube 112 connecting the processed blood collection container 110 and the blood outlet port 107 with each other; the clamp 121 serving as the first duct opening/dosing member and installed on the first tube 111; and the clamp 122 serving as the second duct opening/closing member and installed on the second tube 112.

Figure 12:
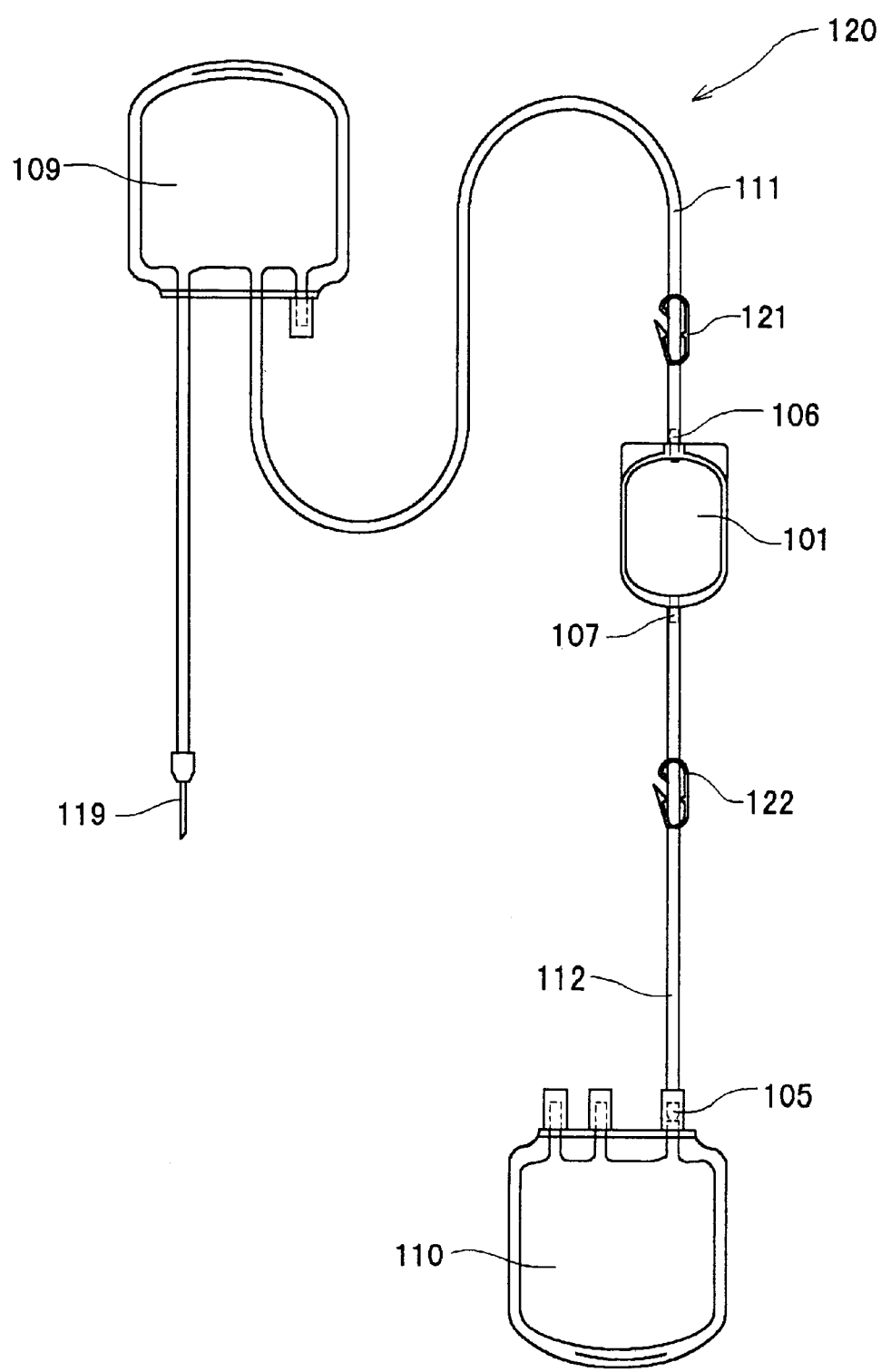
FIG. 12 is an explanatory view showing a white blood cell-removing apparatus of another embodiment of the present invention.

It is possible to use the white blood cell-removing apparatus 120 shown in FIG. 12 having the unprocessed blood filling container 109 connected with one end of the first tube 111 and connected with a blood collection tube provided with a blood collection needle 119 at one end thereof.

The white blood cell-removing method of this invention is a method of manufacturing a white blood cell-removed thick red blood cell product.

As shown in FIG. 13, in performing the white blood cell-removing method of the embodiment, the unprocessed blood filling container 109 is connected with the blood inlet side of the white blood cell-removing device 101 of the white blood cell-removing apparatus 100, and the processed blood collection container 110 made of soft resin is connected with the blood outlet side of the white blood cell-removing device 101.

More specifically, the clamps 121 and 122 of the white blood cell-removing apparatus 100 shown in FIG. 11 are dosed. The connection portion (needle connector) 108 of the white blood cell-removing apparatus 100 is pierced into the discharge opening of the unprocessed blood filling container 109.

Then, with the blood outlet side (blood outlet port or tube connecting the white blood cell-removing device and processed blood collection container with each other) of the white blood cell-removing device 101 closed, a first air-feeding process is performed: The white blood cell-removing device 101 is pressed to feed at least one part of air inside the white blood cell-removing device 101 into the unprocessed blood filling container 109.

More specifically, the clamp 121 is opened-and the white blood cell-removing device 101 is pressed at a slight force to feed the air inside the white blood cell-removing device 101 into the unprocessed blood filling container 109. Then, the clamp 121 is closed. As shown in FIG. 13, the unprocessed blood filling container 109 is hung on the stand 125.

Then, a second air-feeding process is carried out: Blood is introduced into the white blood cell-removing device 101 from the unprocessed blood filling container 109. Then, the air inside the white blood cell-removing device 101 is fed into the processed blood collection container 110 before processed blood flows thereinto.

More specifically, the clamp 122 is opened. Then, turning the white blood cell-removing device 101 upside down, the clamp 121 is opened. As a result, an initial flow of blood is introduced into the white blood cell-removing device 101, and the air (air not eliminated from white blood cell-removing device 101 in first air-feeding process) in the white blood cell-removing device 101 is expelled and introduced into the processed blood collection container 110. After the air in the white blood cell-removing device 101 is expelled and the interior thereof is filled with blood, the white blood cell-removing device 101 is turned downside up, as shown in FIG. 13 to start a white blood cell-removing operation.

The blood inside the unprocessed blood filling container 109 is fed to the processed blood collection container 110 through the white blood cell-removing device 101 to perform the white blood cell-removing operation.

The termination of the white blood cell-removing operation can be confirmed by observing a state in which the blood inside the unprocessed blood filling container 109 flows downward and the air therein reaches the inlet side blood chamber of the white blood cell-removing device 101 through the first tube 111 connected with the lower end of the unprocessed blood filling container 109. By performing the first air-feeding process, it is possible to flow blood present between the unprocessed blood filling container 109 and the inlet side blood chamber of the white blood cell removing device 101 into the white blood cell-removing device 101.

After the white blood cell-removing operation terminates, the air inside the processed blood collection container 110 is fed to the outlet side blood chamber of the white blood cell-removing device 101 or to the second tube 112 or to the outlet side blood chamber of the white blood cell-removing device 101 and the second tube 112 by pressing the processed blood collection container 110. Thereby, the operation of collecting the processed blood inside the outlet side blood chamber of the white blood cell-removing device 101 or the processed blood present in the second tube 112 is performed.

More specifically, after the white blood cell-removing operation terminates, air which has flowed into the processed blood collection container 110 is moved toward the second tube 112 to press the processed blood collection container 110. Consequently, the outlet side blood chamber of the white blood cell-removing device 101 expands, and thus air and a part of the processed blood flow thereinto. When the pressing of the processed blood collection container 110 terminates, the blood staying in the outlet side blood chamber of the white blood cell-removing device 101 and in the second tube 112 flow downward, and air remains in the outlet side blood chamber of the white blood cell-removing device 101 or in the second tube 112. By performing the second air-feeding process and the processed blood collection operation, it is possible to collect the processed blood present in the outlet side blood chamber of the white blood cell-removing device 101 or in the second tube 112 thereby to increase the collection efficiency of blood product. It is preferable to perform the processed blood collection operation, with the clamp 121 closed. By doing so, in feeding out the air present in the processed blood collection container 110, it is possible to prevent the air from being introduced into the inlet side blood chamber of the white blood cell-removing device 101 or prevent that substances trapped by the filter member 5 peel from the filter member.

Then, the clamps 121 and 122 are closed. Then, using tube sealers, the container in which necessary blood product has been collected and other members are sealed and separated from one another. Thereby, all operations of the white blood cell-removing method terminate.

The blood product collected when the three processes, namely, the first air-feeding process, the second air-feeding process, and the processed blood collecting process were performed was more by about 27 ml than that collected when none of the three processes was performed.

Although it is preferable to perform the first air-feeding process, it is possible to obtain a sufficiently favorable effect even though the first air-feeding process is not performed. More specifically, the blood product collected when the first air-feeding process was not performed and the two processes, namely, the second air-feeding process and the processed blood collecting process were performed was more by about 15 ml than that collected when none of the three processes was performed.

Although it is preferable to perform the second air-feeding process and the processed blood collecting process, it is possible to obtain a sufficiently favorable effect even though they are not performed. More specifically, the blood product collected when the first air-feeding process was performed and the second air-feeding process and the processed blood collecting process were not performed was more by about 12 ml than that collected when none of the three processes was performed.

The second embodiment of the white blood cell-removing method of the present invention will be described below.

The white blood cell-removing method of this embodiment is carried out by using a white blood cell-removing apparatus comprising a white blood cell-removing device having a bag-shaped housing made of soft resin; a white blood cell-removing member partitioning an inside of the housing into an inlet side blood chamber and an outlet side blood chamber; a blood inlet port positioned at one side of the housing and communicating with the inlet side blood chamber; and a blood outlet port positioned at the other side of the housing and communicating with the outlet side blood chamber. The white blood cell-removing method is carried out in a state where an unprocessed blood filling container made of soft resin and containing unprocessed blood is connected with the white blood cell-removing device at a blood flow inlet side thereof through a first tube; a processed blood collection container made of soft resin and containing a blood-preserving liquid and collecting treated blood is connected with the white blood cell-removing device at a blood flow outlet side thereof through a second tube; and a blood component collection container made of soft resin is connected with the first tube connecting the white blood cell-removing device and the unprocessed blood filling container with each other. The method comprises the steps of pressing the white blood cell-removing device and the blood component collection container to feed at least one part of air inside the white blood cell-removing device and the blood component collection container to the processed blood collection container in which the blood-preserving liquid has been filled; feeding at least one part of the blood-preserving liquid from the processed blood collection container to the unprocessed blood filling container, together with at least one part of the air in the white blood cell-removing device, by placing the blood inlet side of the white blood cell-removing device at an upward position and the blood outlet side thereof at a downward position; feeding the blood inside the unprocessed blood filling container to the processed blood collection container through the white blood cell-removing device, by placing the blood inlet side of the white blood cell-removing device at an upward position and the blood outlet side thereof at a downward position, and placing an outlet side of the unprocessed blood filling container at a downward position such that the outlet side of the unprocessed blood filling container is located at a level higher than the white blood cell-removing device; feeding air inside the processed blood collection container to the outlet side blood chamber of the white blood cell-removing device or to the second tube or to the outlet side blood chamber and the second tube by pressing the-processed blood collection container; and collecting processed blood present in the outlet side blood chamber of the white blood cell-removing device or in the second tube or in the outlet side blood chamber and the second tube into the processed blood collection container.

Figure 14:
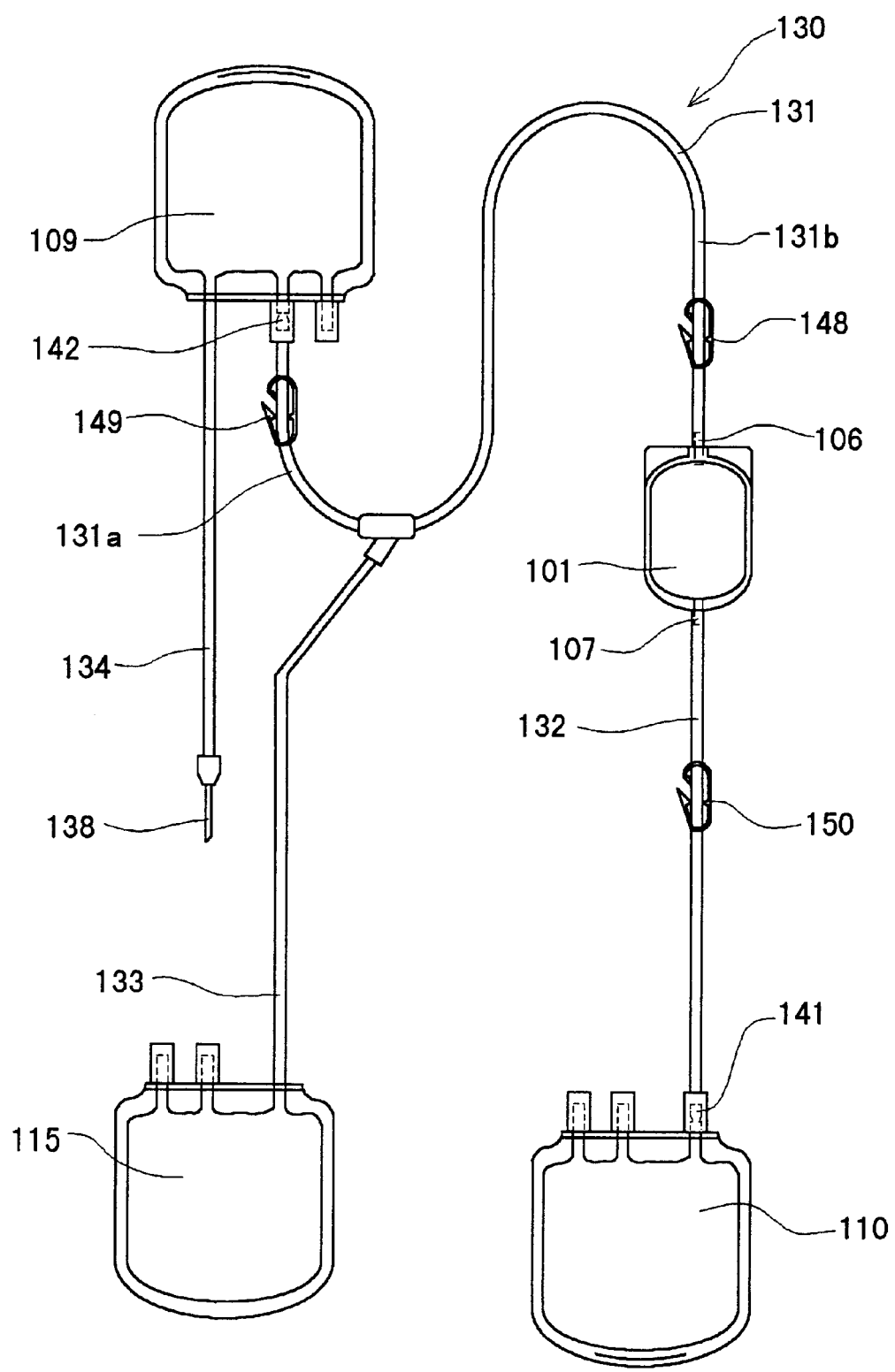
FIG. 14 is an explanatory view showing a white blood cell-removing method of the present invention.

In performing the white blood cell-removing method of the embodiment, a white blood cell-removing apparatus 130 shown in FIG. 14 is used.

The white blood cell-removing apparatus 130 includes the white blood cell-removing device 101 comprising the housing made of soft resin; the white blood cell-removing member partitioning the inside of the housing into the inlet side blood chamber and the outlet side blood chamber, the blood inlet port 106 positioned at one side of the housing and communicating with the inlet side blood chamber and the blood outlet port 107 positioned at the other side of the housing and communicating with the outlet side blood chamber; the unprocessed blood filling container 109; a first tube 131 connecting the blood inlet port 106 and the unprocessed blood filling container 109 with each other; the processed blood collection container 110 made of soft resin and containing a blood-preserving liquid; a second tube 132 connecting the processed blood collection container 110 and the blood outlet port 107 with each other; a blood component collection container 115 connected with the first tube 131 through a third tube 133; and a blood collection tube 134 connected with the unprocessed blood filling container 109 and having a blood collection needle 138 at an end thereof. A clamp may be installed on each of the first and second tubes 131 and 132. Further, the white blood cell-removing apparatus has a breakable first duct regulation member 141 closing a portion between the inside of the processed blood collection container 110 and the second tube 132. The white blood cell-removing apparatus has also a breakable second duct regulation member 142 closing a portion between the inside of the unprocessed blood filling container 109 and the first tube 131.

The white blood cell-removing method of this-invention is a method of manufacturing a white blood cell-removed thick red blood cell product.

In performing the white blood cell-removing method of the embodiment, the white blood cell-removing apparatuses shown in FIG. 14 is used.

Initially, the blood collection needle 138 is pierced into a donor to collect blood into the unprocessed blood filling container 109. Using a sealer, the blood collection tube 134 is cut for sealing near the unprocessed blood filling container 109, and a part of thereof located at the blood collection needle side is discarded. The blood is left at the room temperature for six hours. The white blood cell-removing apparatus 130 is centrifuged.

Then, a first air-feeding process is performed: The white blood cell-removing device 101 and the blood component collection container 115 are pressed to feed at least one part of air present therein into the processed blood collection container 110 in which the blood-preserving liquid has been filled.

The unprocessed blood filling container 109 is hung on a hanger portion of a blood separation stand (not shown). The processed blood collection container 110 is placed at a lowermost position and the first duct regulation member 141 is broken to communicate the interior of the processed blood collection container 110 with the second tube 132. Then, the white blood cell-removing device 101 and the blood component collection container 115 are pressed to feed air into the processed blood collection container 110. After a part 131b of the first tube 131 is sealed with the clamp 148, the second duct regulation member 142 is broken to communicate the interior of the unprocessed blood filling container 109 with the first tube 131. Then, by operating the blood separation stand, the unprocessed blood filling container 109 is pressed to feed blood plasma obtained as a supernatant liquid therein to the blood component collection container 115. After the feeding of the supernatant liquid is completed, a part 131a of the first tube 131 is closed with the clamp 149. Then, the third tube 133 is cut for sealing with a sealer to cut off the blood component collection container 115 The blood component collection container 115 is refrigerated.

Then, an air-preserving liquid feeding process is performed: At least one part of the blood-preserving liquid is fed from the processed blood collection container 110 to the unprocessed blood filling container 109, together with at least one part of air remaining in the white blood cell-removing device 101, by placing the blood inlet side of the white blood cell-removing device 101 at an upward position and the blood outlet side thereof at a downward position.

Figure 15:
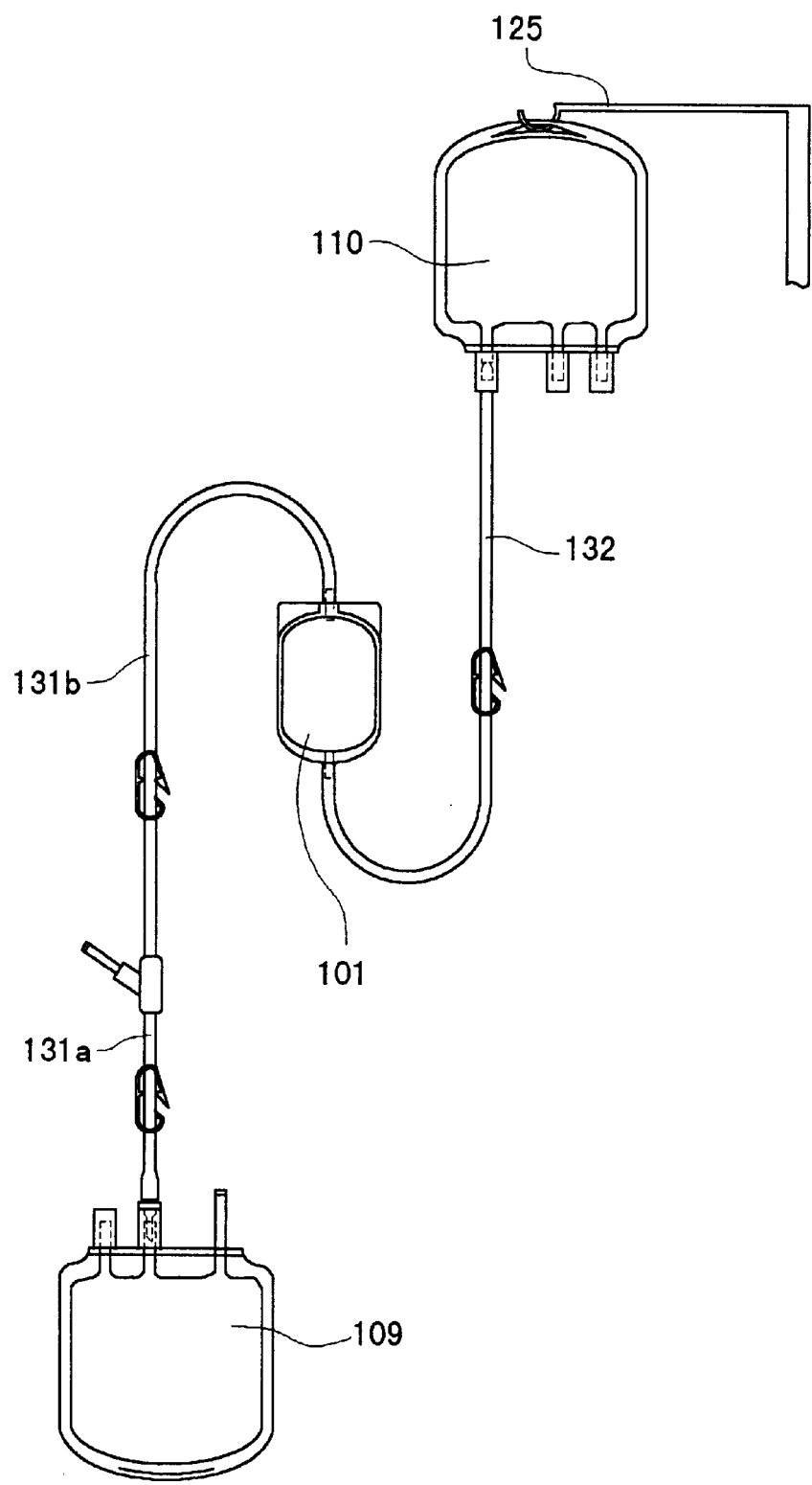
FIG. 15 is an explanatory view showing a white blood cell-removing method of the present invention.

More specifically, as shown in FIG. 15, the processed blood collection container 110 is hung at a position of a high level, and the unprocessed blood filling container 109 is placed at a downward position. The white blood cell-removing device 101 is turned upside down. Then, the clamp 148 sealing the part 131b of the first tube 131 and the damp 150 sealing the second tube 132 are opened. Thereby, the blood-preserving liquid (for example, SAGM liquid) flows into the white blood cell-removing device 101. As a result, air (air not eliminated in first air-feeding process and remaining in white blood cell-removing device 101) inside the white blood cell-removing device 101 is expelled therefrom and introduced into the unprocessed blood filling container 109. When the air inside the white blood cell-removing device 101 is expelled and the interior of the white blood cell-removing device is filled with the blood-preserving liquid, the white blood cell-removing device is turned downside up, and almost all of the blood-preserving liquid is flowed into the unprocessed blood filling container 109. Then, the part 131*a* of the first tube 131 is sealed with the clamp 149.

Then, a white blood cell-removing operation is performed: The blood inlet side of the white blood cell-removing device 101 is placed at an upward position, and the blood outlet side thereof is placed at a downward position. The blood outlet side of the unprocessed blood filling container 109 is placed at a downward position such that the blood outlet side thereof is located at a level higher than the white blood cell-removing device 101. The processed blood collection container 110 is placed at a level lower than the white blood cell-removing device 101. The blood inside the unprocessed blood filling container 109 is fed to the processed blood collection container 110 through the white blood cell-removing device 101.

Figure 16:
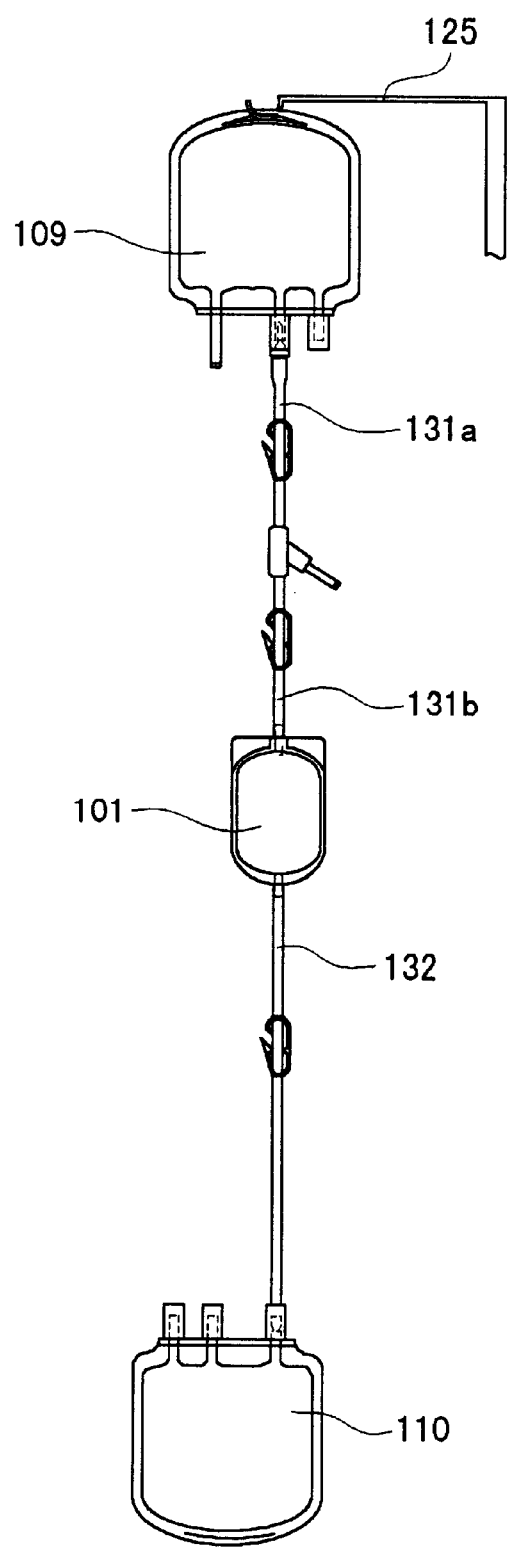
FIG. 16 is an explanatory view showing a white blood cell-removing method of the present invention.

More specifically, after the content of the unprocessed blood filling container 109 is stirred gently, the unprocessed blood filling container 109 is hung at a high location as shown in FIG. 16; the clamp 149 which has sealed the part 131*a* of the first tube 131 is opened; the blood-preserving liquid-added blood is passed through the white blood cell-removing device 101; and the processed blood is collected by the processed blood collection container 110. The termination of the white blood cell-removing operation can be confirmed by observing a state in which the blood flows downward inside the unprocessed blood filling container 109 and air inside it arrives at the inlet side blood chamber of the white blood cell-removing device 101 through the tube located below the unprocessed blood filling container 109. It is possible to flow the blood present between the unprocessed blood filling container 109 and the inlet side blood chamber of the white blood cell-removing device 101 into the white blood cell-removing device 101 by performing the first air-feeding process.

Then, a processed blood collection process is performed: By pressing the processed blood collection container 110, air therein is fed to the outlet side blood chamber of the white blood cell-removing device 101 or to the second tube 132 or to the outlet side blood chamber of the white blood cell-removing device 101 and the second tube to collect the processed blood present in the outlet side blood chamber of the white blood cell-removing device 101 or to the second tube 132 or to the outlet side blood chamber of the white blood cell-removing device 101 and the second tube.

After the white blood cell-removing operation terminates, air inside the processed blood collection container 110 is moved toward the second tube 132 to press the processed blood collection container 110. Consequently, the outlet side blood chamber of the white blood cell-removing device 101 expands and thus air and a part of the processed blood flow thereinto. When the pressing of the processed blood collection container 110 terminates, blood staying in the outlet side blood chamber of the white blood cell-removing device 101 and blood staying in the second tube 132 flow downward, and air remains in the outlet side blood chamber of the white blood cell-removing device 101 or/and the second tube 132. It is possible to collect the processed blood present in the outlet side blood chamber of the white blood cell-removing device 101 or/and in the second tube 132 by performing the air-preserving liquid feeding process and the processed blood collection process. Thus, the second white blood cell-removing method increases the collection efficiency of the blood product. It is preferable to perform the processed blood collection process by closing the clamp 148 installed on the part 131*b* of the first tube 131 or the clamp 149 installed on the part 131*a* of the first tube 131. By doing so, when air is fed out from the processed blood collection container 110, it is possible to prevent the air therein from flowing into the inlet side blood chamber of the white blood cell-removing device 101 or prevent that substances trapped by the filter member peel from the filter member.

Then, using a tube sealer or the like, the second tube 132 is cut for sealing to cut off the processed blood collection container 110 from the second tube 132. The processed blood collection container 110 is then refrigerated.

The blood product collected when the three processes, namely, the first air-feeding process, the air-preserving liquid feeding process, and the processed blood collecting process were performed was more by about 27 ml than that collected when none of the three processes was performed.

Although it is preferable to perform the first air-feeding process, it is possible to obtain a sufficiently favorable effect even though the first air-feeding process is not performed. More specifically, the blood product collected when the first air-feeding process was not performed and the two processes, namely, the air-preserving liquid feeding process and the processed blood collection process were performed was more by about 14 ml than that collected when none of the three processes was performed.

Although it is preferable to perform the second air-feeding process and the processed blood collecting process, it is possible to obtain a sufficiently favorable effect even though they are not performed. More specifically, the blood product collected when the first air-feeding process was performed and the air-preserving liquid feeding process and the processed blood collecting process were not performed was more by about 13 ml than that collected when none of the three processes was performed.

The white blood cell-removing apparatus to be used in the embodiment has the blood component collection container 115 connected with the first tube 131 through the third tube 133. But the white blood cell-removing apparatus does not necessarily have the blood component collection container 115. Needless to say, in the case where the white blood cell-removing apparatus does not have the blood component collection container 115, the operation (process) relating to the blood component collection container 115 is omitted.

It is preferable that in the above-described white blood cell-removing method, the white blood cell-removing device 101 preserves 5 ml or more of air therein.

What is claimed is:

1. A white blood cell-removing device comprising:
   a bag-shaped housing made of soft resin;
   a white blood cell-removing filter member partitioning an inside of said housing into an inlet side blood chamber and an outlet side blood chamber;
   a blood inlet port positioned at one side of said housing and communicating with said inlet side blood chamber; and
   a blood outlet port positioned at the other side of said housing and communicating with said outlet side blood chamber,
   wherein an unevenness surface having a difference of 0.2–2 mm between highest and lowest portions thereof is formed on an inner surface of said bag-shaped housing made of soft resin and confronting said outlet side blood chamber,
   wherein said white blood cell-removing filter member has a filtering part and a non-filtering part formed on an entire periphery of said filtering part; and a blood duct formed between said non-filtering part and an inner surface of said housing is located on an inner peripheral part of said housing, and wherein said unevenness surface is formed of a plurality of lengthwise ribs extending from a blood inlet port side of said housing to a blood outlet port side of said housing and a plurality of widthwise ribs intersecting substantially perpendicularly with said lengthwise ribs, and a height of each of said widthwise ribs is smaller than that of each of said lengthwise ribs, and said widthwise ribs are spaced at larger intervals than said lengthwise ribs.

2. A white blood cell-removing device according to claim 1, wherein said widthwise ribs are spaced at intervals of 1–5 mm.

3. A white blood cell-removing device according to claim 1, wherein either or both of lengthwise and widthwise said ribs consist of scattered projections.

4. A white blood cell-removing device according to claim 1, wherein said lengthwise ribs are spaced at intervals of 1–5 mm.

5. A white blood cell-removing device according to claim 1, wherein a filtering part of said white blood cell-removing filter member is formed of a filtering material of a porous material or nonwoven cloth.

6. A white blood cell-removing device according to claim 5, wherein said filtering material comprises porous material which is made of polyurethane.

7. A white blood cell-removing device according to claim 5, wherein said filtering material comprises nonwoven cloth which is made of polyester fibers.

8. A white blood cell-removing device according to claim 1, wherein said bag-shaped housing made of soft resin consists of two thermoplastic soft resinous sheets; said white blood cell-removing filter member consists of a sheet-shaped frame made of thermoplastic soft resin and a filtering material whose peripheral portion is fixed to said sheet-shaped frame; said white blood cell-removing filter member is sandwiched between said two thermoplastic soft resinous sheets; and a peripheral portion of said sheet-shaped frame made of thermoplastic soft resin is thermally fused to said two thermoplastic soft resinous sheets.

9. A white blood cell-removing apparatus comprising:
a white blood cell-removing device comprising a housing made of soft resin, a white blood cell-removing member partitioning an inside of said housing into an inlet side blood chamber and an outlet side blood chamber, a blood inlet port positioned at one side of said housing and communicating with said inlet side blood chamber and a blood outlet port positioned at the other side of said housing and communicating with said outlet side blood chamber;
a first tube connecting to said blood inlet port;
a processed blood collection container made of soft resin; and
a second tube connecting said processed blood collection container and said blood outlet port with each other,
wherein said processed blood collection container is adapted to preserve air in an amount more than the sum of a volume of said outlet side blood chamber of said white blood cell-removing device and a volume of said second tube.

10. A white blood cell-removing apparatus according to claim 9, wherein said white blood cell-removing apparatus has a flow-out restraining part for restraining air filling said processed blood collection container from flowing out from said white blood cell-removing apparatus.

11. A white blood cell-removing apparatus according to claim 10, wherein said flow-out restraining part for restraining air filling said processed blood collection container from flowing out from said white blood cell-removing apparatus is provided on said first tube, said second tube or at a portion where said second tube and said processed blood collection container are connected with each other.

12. A white blood cell-removing apparatus according to claim 9, wherein said first tube has a first duct opening/closing member; and said second tube has a second duct opening/closing member.

13. A white blood cell-removing apparatus according to claim 12, wherein said flow-out restraining part for restraining air filling said processed blood collection container from flowing out from said white blood cell-removing apparatus is said first duct opening/closing member in a closed state or said second duct opening/closing member in a closed state.

14. A white blood cell-removing apparatus according to claim 9, wherein said white blood cell-removing device preserves air in an amount of 5 ml or more.

15. A white blood cell-removing apparatus according to claim 9, wherein said white blood cell-removing apparatus has a third tube connecting said first tube to a blood component collection container.

16. A white blood cell-removing apparatus according to claim 9, wherein said white blood cell-removing apparatus has an unprocessed blood filling container connecting to said first tube.

17. A white blood cell-removing apparatus according to claim 9, wherein said white blood cell-removing apparatus has a connection portion provided to one end of said first tube for connecting with an unprocessed blood filling container.

18. A white blood cell-removing method which is carried out by using a white blood cell-removing device having: a bag-shaped housing made of soft resin; a white blood cell-removing member partitioning an inside of said housing into an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, said white blood cell-removing method being carried out in a state where an unprocessed blood filling container containing unprocessed blood is connected with said white blood cell-removing device at a blood flow inlet side thereof through a first tube, and a processed-blood collection container made of soft resin and collecting treated blood is connected with said white blood cell-removing device at a blood flow outlet side thereof through a second tube, said method comprising the steps of:
introducing blood into said white blood cell-removing device from said unprocessed blood filling container;
feeding air inside said white blood cell-removing device to said processed blood collection container;
feeding said blood contained in said unprocessed blood filling container to said processed blood collection container by passing said blood through said white blood cell-removing device; and
feeding air in said processed blood collection container to said outlet side blood chamber of said white blood cell-removing device and/or to said second tube by pressing said processed blood collection container; and collecting processed blood from said outlet side blood chamber of said white blood cell-removing device and/or processed blood from said second tube in said processed blood collection container.

19. A white blood cell-removing method which is carried out by using a white blood cell-removing device having: a bag-shaped housing made of soft resin; a white blood cell-removing member partitioning an inside of said housing into an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, said white blood cell-removing method being carried out in a state where an unprocessed blood filling container containing unprocessed blood is connected with said white blood cell-removing device at a blood flow inlet side thereof through a first tube, and a processed blood collection container collecting treated blood is connected with said white blood cell-removing device at a blood flow outlet side thereof through a second tube, said method comprising the steps of:
pressing said white blood cell-removing device;
feeding at least one part of air inside said white blood cell-removing device to said unprocessed blood filling container;
collecting processed blood in said processed blood collection container by passing blood contained in said unprocessed blood filling container through said white blood cell-removing device.

20. A white blood cell-removing method according to claim 19, further comprises the step of feeding said air inside said processed blood collection container to said outlet side blood chamber of said white blood cell-removing device and/or to said second tube by pressing said processed blood collection container after the step of collecting processed blood; and
collecting processed blood from said outlet side blood chamber of said white blood cell-removing device and/or processed blood from said second tube or processed blood from said outlet side blood chamber and said second tube in said processed blood collection container.

21. A white blood cell-removing method which is carried out by using a white blood cell-removing device having: a bag-shaped housing made of soft resin; a white blood cell-removing member partitioning an inside of said housing into an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, said white blood cell-removing method being carried out in a state where an unprocessed blood filling container containing unprocessed blood is connected with said white blood cell-removing device at a blood flow inlet side thereof through a first tube, and a processed blood collection container made of soft resin and containing a blood-preserving liquid and collecting treated blood is connected with said white blood cell-removing device at a blood flow outlet side thereof through a second tube, said method comprising the steps of:
feeding at least one part of said blood-preserving liquid from said processed blood collection container to said unprocessed blood filling container, together with at least one part of air in said white blood cell-removing device;
feeding blood inside said unprocessed blood filling container to said processed blood collection container through said white blood cell-removing device;
feeding air inside said processed blood collection container to said outlet side blood chamber of said white blood cell-removing device and/or to said second tube by pressing said processed blood collection container; and
collecting processed blood from said outlet side blood chamber of said white blood cell-removing device and/or processed blood from said second tube in said processed blood collection container.

22. A white blood cell-removing method which is carried out by using a white blood cell-removing device having: a bag-shaped housing made of soft resin; a white blood cell-removing member partitioning an inside of said housing in an inlet side blood chamber and an outlet side blood chamber; a blood inlet port positioned at one side of said housing and communicating with said inlet side blood chamber; and a blood outlet port positioned at the other side of said housing and communicating with said outlet side blood chamber, said white blood cell-removing method being carried out in a state where an unprocessed blood filling container containing unprocessed blood is connected with said white blood cell-removing device at a blood flow inlet side thereof through a first tube; a processed blood collection container made of soft resin and containing a blood-preserving liquid and collecting treated blood is connected with said white blood cell-removing device at a blood flow outlet side thereof through a second tube, said method comprising the steps of:
pressing said white blood cell-removing device to feed at least one part of air inside said white blood cell-removing device to said processed blood collection container in which said blood-preserving liquid has been filled;
feeding blood inside said unprocessed blood filling container to said processed blood collection container through said white blood cell-removing device.

23. A white blood cell-removing method according to claim 22, further comprises the step of feeding air inside said processed blood collection container to said outlet side blood chamber of said white blood cell-removing device and/or to said second tube by pressing said processed blood collection container after the step of feeding blood; and
collecting processed blood from said outlet side blood chamber of said white blood cell-removing device and/or processed blood from said second tube in said processed blood collection container.

24. A white blood cell-removing method according to claim 22, wherein said white blood cell-removing apparatus has a blood component collection container made of soft resin connected with said white blood cell removing device and said blood component collection container is pressed together with said white blood cell-removing device in the step of pressing said white blood cell-removing device.

* * * * *

UNITED STATES PATENT AND TRADEMARK OFFICE
CERTIFICATE OF CORRECTION

PATENT NO. : 6,221,264 B1
DATED : April 24, 2001
INVENTOR(S) : Noboru Ishida, et al.

It is certified that error appears in the above-identified patent and that said Letters Patent is hereby corrected as shown below:

<u>Title page,</u>
Item [30], the Foreign Application Priority Data is changed to read:
-- May 19, 1998    (JP) ........................ 10-155232 --

<u>Column 13,</u>
Line 40, is changed to read:
-- Number of white blood cells (x$10^7$)    227 ± 22    265 ± 25    210 ± 28 --

<u>Column 14,</u>
Line 5, is changed to read:
-- Number of platelets (x$10^9$)    11 ± 2    12 ± 3 --

Claim 3, is corrected to read:
-- 3. A white blood cell-removing device according to claim 1, wherein either or both of said lengthwise and widthwise ribs consist of scattered projections. --

Signed and Sealed this

Thirteenth Day of November, 2001

*Attest:*

*Attesting Officer*

NICHOLAS P. GODICI
*Acting Director of the United States Patent and Trademark Office*